US012661014B2

(12) United States Patent
Liu et al.

(10) Patent No.: US 12,661,014 B2
(45) Date of Patent: Jun. 23, 2026

(54) SYSTEMS AND METHODS FOR TEMPERATURE MEASUREMENT

(71) Applicant: ZHEJIANG PIXFRA TECHNOLOGY CO., LTD., Hangzhou (CN)

(72) Inventors: Su Liu, Hangzhou (CN); Ziwei Wei, Hangzhou (CN); Diquan Xu, Hangzhou (CN); Tao Pu, Hangzhou (CN); Zhiqiang Yang, Hangzhou (CN); Jie Zhan, Hangzhou (CN); Wuping Lu, Hangzhou (CN)

(73) Assignee: ZHEJIANG PIXFRA TECHNOLOGY CO., LTD., Hangzhou (CN)

( * ) Notice: Subject to any disclaimer, the term of this patent is extended or adjusted under 35 U.S.C. 154(b) by 833 days.

(21) Appl. No.: 18/154,085

(22) Filed: Jan. 13, 2023

(65) Prior Publication Data

US 2023/0172457 A1     Jun. 8, 2023

Related U.S. Application Data

(63) Continuation of application No. PCT/CN2021/108216, filed on Jul. 23, 2021.

(30) Foreign Application Priority Data

Jul. 27, 2020 (CN) .......................... 202010730901.1

(51) Int. Cl.
A61B 5/00 (2006.01)
A61B 5/01 (2006.01)
(Continued)

(52) U.S. Cl.
CPC .................. A61B 5/01 (2013.01); G06T 7/60 (2013.01); G06T 7/70 (2017.01); G06V 10/25 (2022.01);
(Continued)

(58) Field of Classification Search
CPC .... A61B 5/01; G06T 7/60; G06T 7/70; G06T 2207/20081; G06T 2207/30201;
(Continued)

(56) References Cited

U.S. PATENT DOCUMENTS

2017/0248478 A1     8/2017  Yen et al.
2018/0073930 A1 *   3/2018  Meggers .................. G01K 3/06
(Continued)

FOREIGN PATENT DOCUMENTS

CN          109846463 A     6/2019
CN          111297337 A     6/2020
(Continued)

OTHER PUBLICATIONS

International Search Report in PCT/CN2021/108216 mailed on Oct. 21, 2021, 4 pages.
(Continued)

*Primary Examiner* — May A Abouelela
(74) *Attorney, Agent, or Firm* — Metis IP LLC

(57) ABSTRACT

A method for temperature measurement may be provided. The method may include obtaining an image of an object acquired by an imaging device. The method may also include determining an angle between the object and the imaging device based on the image. The angle may be defined by a reference direction and a direction that the object is facing. The method may further include determining a temperature of the object in response to determining that the angle satisfies a condition based on the image.

17 Claims, 9 Drawing Sheets

(51) Int. Cl.

| | | |
|---|---|---|
| *G06T 7/60* | (2017.01) | |
| *G06T 7/70* | (2017.01) | |
| *G06V 10/25* | (2022.01) | |
| *G06V 10/44* | (2022.01) | |
| *G06V 10/70* | (2022.01) | |

(52) U.S. Cl.
CPC .............. *G06V 10/44* (2022.01); *G06V 10/70* (2022.01); *G06T 2207/20081* (2013.01); *G06T 2207/30201* (2013.01)

(58) Field of Classification Search
CPC ........... G06T 7/344; G06T 7/75; G06V 10/25; G06V 10/44; G06V 10/70; G06V 10/82; G06V 40/161; G06V 40/168; G01J 5/025; G01J 5/026; G01J 5/0275; G01J 2005/0077; G01J 5/0025
See application file for complete search history.

(56) References Cited

U.S. PATENT DOCUMENTS

| | | | | |
|---|---|---|---|---|
| 2018/0122117 | A1* | 5/2018 | Kawano | G06T 7/60 |
| 2018/0238740 | A1* | 8/2018 | Christel | H04N 23/23 |
| 2019/0347763 | A1* | 11/2019 | Goel | G06T 3/053 |
| 2019/0349562 | A1* | 11/2019 | Oh | G06T 7/70 |
| 2019/0365299 | A1* | 12/2019 | Carroll | A61B 5/14521 |
| 2020/0256734 | A1 | 8/2020 | Zhu et al. | |
| 2021/0248353 | A1 | 8/2021 | Yu et al. | |
| 2021/0364487 | A1* | 11/2021 | Zhang | G01J 5/00 |
| 2021/0368075 | A1* | 11/2021 | Takeuchi | G01S 17/42 |
| 2021/0390729 | A1* | 12/2021 | Fox-Roberts | G06T 7/73 |
| 2022/0004760 | A1* | 1/2022 | Kozachenok | A01K 61/80 |
| 2022/0038644 | A1* | 2/2022 | McAllister | G06V 20/13 |
| 2022/0167820 | A1* | 6/2022 | Wu | G06V 20/50 |
| 2022/0175210 | A1* | 6/2022 | Choi | G01B 11/254 |
| 2022/0180571 | A1* | 6/2022 | Ozaki | G09G 5/38 |
| 2022/0253144 | A1* | 8/2022 | Hu | G06Q 20/3274 |

FOREIGN PATENT DOCUMENTS

| | | |
|---|---|---|
| CN | 111339951 A | 6/2020 |
| CN | 111426388 A | 7/2020 |
| TW | M277919 U | 10/2005 |
| WO | 2022022425 A1 | 2/2022 |

OTHER PUBLICATIONS

Written Opinion in PCT/CN2021/108216 mailed on Oct. 21, 2021, 6 pages.

* cited by examiner

<u>200</u>

300

<u>500</u>

<u>600</u>

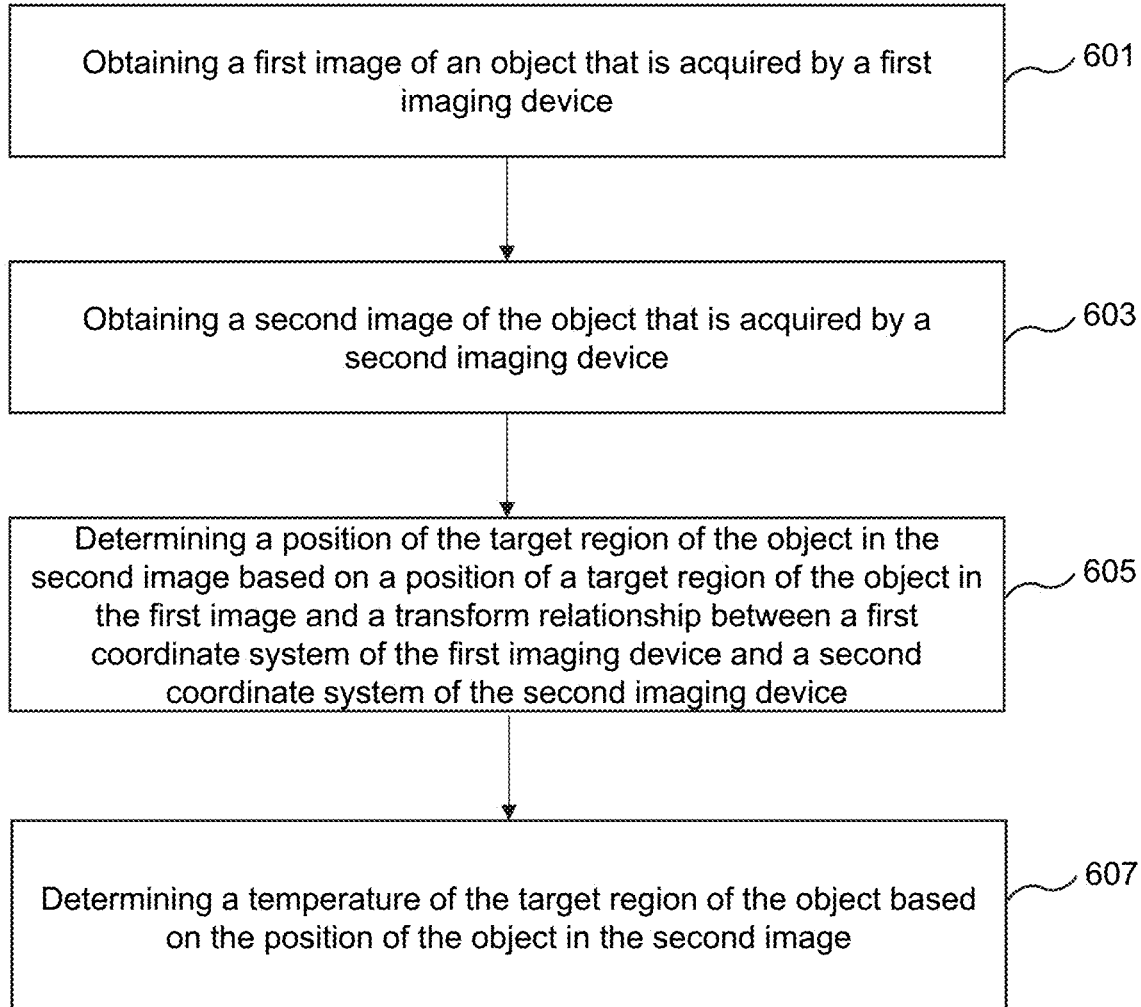

Obtaining a first image of an object that is acquired by a first imaging device    601

Obtaining a second image of the object that is acquired by a second imaging device    603

Determining a position of the target region of the object in the second image based on a position of a target region of the object in the first image and a transform relationship between a first coordinate system of the first imaging device and a second coordinate system of the second imaging device    605

Determining a temperature of the target region of the object based on the position of the object in the second image    607

Figure 7:
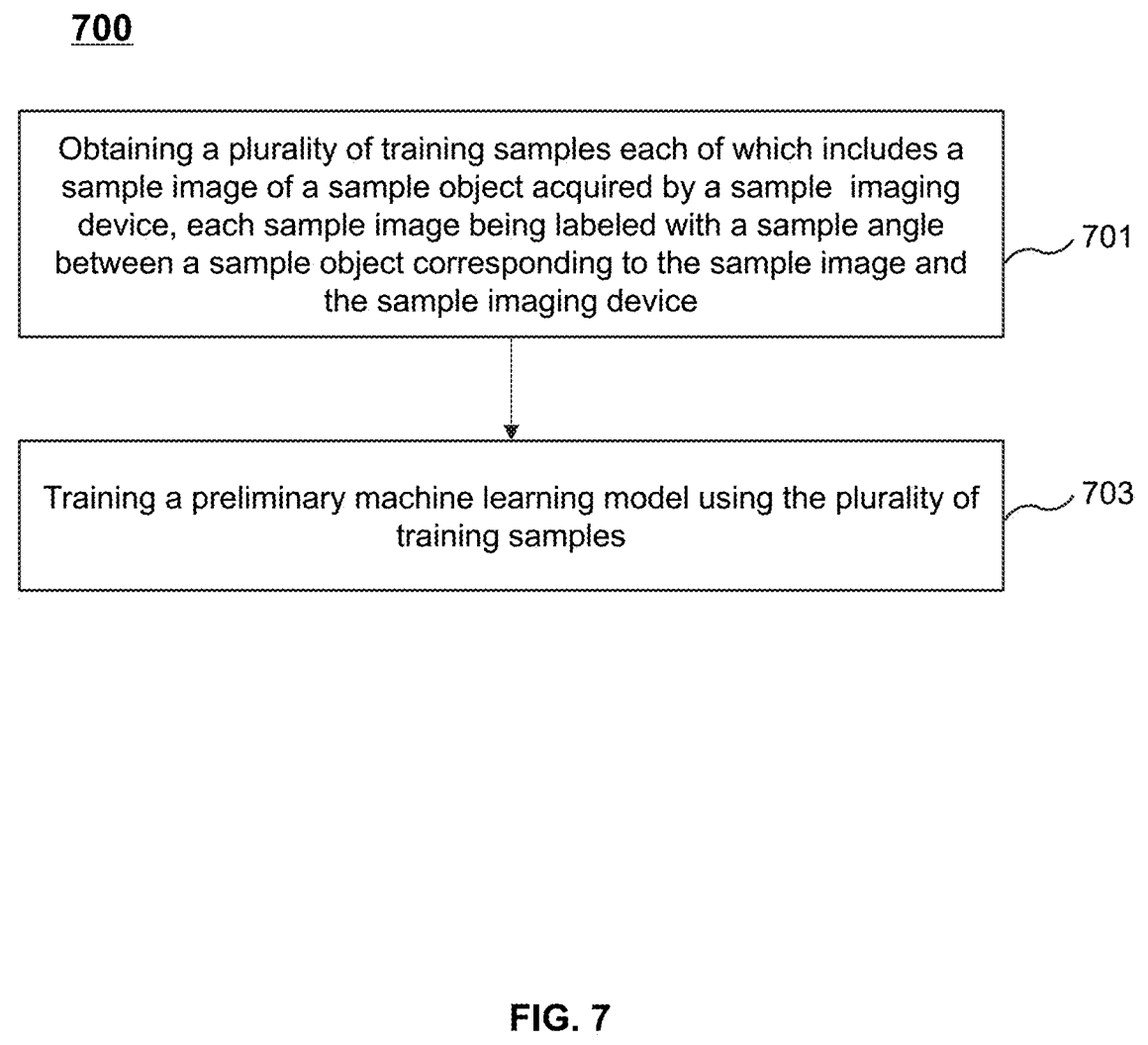

Obtaining a plurality of training samples each of which includes a sample image of a sample object acquired by a sample imaging device, each sample image being labeled with a sample angle between a sample object corresponding to the sample image and the sample imaging device　　701

Training a preliminary machine learning model using the plurality of training samples　　703

SYSTEMS AND METHODS FOR TEMPERATURE MEASUREMENT

CROSS-REFERENCE TO RELATED APPLICATIONS

This application is a continuation of International Application No. PCT/CN2021/108216, filed on Jul. 23, 2021, which claims priority to Chinese Patent Application No. 202010730901.1, filed on Jul. 27, 2020, the contents of which are hereby incorporated by reference.

TECHNICAL FIELD

The present disclosure generally relates to measurement fields, and specifically, to systems and methods for temperature measurement.

BACKGROUND

An accurate body temperature measurement is vital for diagnosis of diseases (e.g., Corona Virus Disease 2019, COVID-19). For example, in prevention and control of the COVID-19, temperature measurement is an efficient approach for confirming suspected infected human beings. A temperature range of a human being is small, such as between 30° C. and 45° C., and the accuracy of the body temperature needs to be high, so as to distinct between suspected infected human beings and normal human beings. Specially, in public areas such as airports, train stations, schools, shopping malls, etc., there is thick stream of people. Accordingly, how to measure the temperature of human beings accurately and efficiently is vital for epidemic prevention and control. Thus, it is desirable to provide systems and methods for temperature measurement with improved accuracy and efficiency.

SUMMARY

According to an aspect of the present disclosure, a system for temperature measurement may be provided. The system may include at least one storage device and at least one processor configured to communicate with the at least one storage device. The at least one storage device may include a set of instructions. When the at least one storage device execute the set of instructions, the at least one processor may be directed to cause the system to perform one or more of the following operations. The system may obtain an image of an object acquired by an imaging device. The system may also determine an angle between the object and the imaging device based on the image. The angle may be defined by a reference direction and a direction that the object is facing. The system may further determine a temperature of the object based on the image in response to determining that the angle satisfies a condition.

In some embodiments, to determine an angle between the object and the imaging device based on the image, the system may determine the angle between the object and the imaging device based on the image using an angle detection model associated with a plurality of reference images of reference objects each of which is acquired by a reference imaging device and corresponds to a reference angle between a reference object and the reference imaging device.

In some embodiments, the angle detection model may include a trained machine learning model. To train the machine learning model, the system may obtain the plurality of reference images of reference objects. The system may also label each of at least a portion of the plurality of reference images with the reference angle corresponding to the reference image. The system may further train a preliminary machine learning model using the plurality of reference images and the reference angles corresponding to the plurality of reference images.

In some embodiments, to determine an angle between the object and the imaging device based on the image, the system may input the image into the trained machine learning model. The system may also extract image features from the image using the trained machine learning model. The system may further determine the angle based on the image features from the image.

In some embodiments, the angle detection model may include a corresponding relationship between each of the plurality of reference images of reference objects and the reference angle between the reference object and the imaging device. To determine an angle between the object and the imaging device based on the image using an angle detection model, the system may extract angle features from the image. The system may extract reference angle features from each of the plurality of reference images. The system may also determine at least one of the plurality of reference images whose reference angle features match the angle features of the image. The system may further determine the angle between the object and the imaging device based on at least one reference angle corresponding to the at least one of the plurality of reference images.

In some embodiments, the at least one processor may be also directed to cause the system to perform one or more of the following operations. The system may obtain an additional image of the object acquired by the imaging device and an additional angle between the object and the imaging device when the imaging device acquires the additional image. The system may further determine the temperature of the object based on the additional image in response to determining that the additional angle satisfies the condition.

In some embodiments, to determine the temperature of the object based on the image, the system may identify a target region of the object from the image. The system may further determine the temperature of the object based on temperature information of the target region.

In some embodiments, the target region may include at least one of a facial area or a forehead area.

In some embodiments, to determine the temperature of the object based on temperature information of the target region, the system may determine a bounding box enclosing the target region. The bounding box may be defined by at least one of one or more geometric parameters and position parameters. The system may further determine the temperature of the object based on the temperature information of the target region enclosed by the bounding box.

In some embodiments, to determine the temperature of the object based on the image, the system may obtain a second image of the object acquired by a second imaging device. The second image may include temperature information of the object. The system may determine a position of the object in the second image based on a position of the object in the image and a transform relationship between a first coordinate system of the imaging device and a second coordinate system of the second imaging device. The system may also obtain the temperature information of the object based on the position of the object in the second image. The system may further determine the temperature of the object based on the temperature information of the object.

According to another aspect of the present disclosure, a system for temperature measurement may be provided. The system may include at least one storage device and at least one processor configured to communicate with the at least one storage device. The at least one storage device may include a set of instructions. When the at least one storage device execute the set of instructions, the at least one processor may be directed to cause the system to perform one or more of the following operations. The system may obtain an image of an object acquired by an imaging device. The system may also determine whether a target region of the object exists in the image. The system may further determine a temperature of the object based on the target region of the object in the image in response to determining that the target region of the object exists in the image.

According to yet another aspect of the present disclosure, a system for temperature measurement may be provided. The system may include at least one storage device and at least one processor configured to communicate with the at least one storage device. The at least one storage device may include a set of instructions. When the at least one storage device execute the set of instructions, the at least one processor may be directed to cause the system to perform one or more of the following operations. The system may obtain an image of an object acquired by an imaging device. The system may also determine whether the image satisfies a condition. The system may further determine a temperature of the object based on the image in response to determining that the image satisfies the condition.

According to yet another aspect of the present disclosure, a method for temperature measurement may be provided. The method may include obtaining an image of an object acquired by an imaging device. The method may also include determining an angle between the object and the imaging device based on the image. The angle may be defined by a reference direction and a direction that the object is facing. The method may further include determining a temperature of the object in response to determining that the angle satisfies a condition based on the image.

According to yet another aspect of the present disclosure, a method for temperature measurement may be provided. The method may include obtaining an image of an object acquired by an imaging device. The method may also include determining whether a target region of the object exists in the image. The method may further include determining a temperature of the object based on the target region of the object in the image in response to determining that the target region of the object exists in the image.

According to yet another aspect of the present disclosure, a method for temperature measurement may be provided. The method may include obtaining an image of an object acquired by an imaging device. The method may also include determining whether the image satisfies a condition. The method may further include determining a temperature of the object based on the image in response to determining that the image satisfies the condition.

According to yet another aspect of the present disclosure, a system for temperature measurement may be provided. The system may include an acquisition module and a determination module. The acquisition module may be configured to obtain an image of an object acquired by an imaging device. The determination module may be configured to determine an angle between the object and the imaging device based on the image. the angle may be defined by a reference direction and a direction that the object is facing. The determination module may be also configured to determine a temperature of the object based on the image in response to determining that the angle satisfies a condition.

According to yet another aspect of the present disclosure, a system for temperature measurement may be provided. The system may include an acquisition module and a determination module. The acquisition module may be configured to obtain an image of an object acquired by an imaging device. The determination module may be configured to determine whether a target region of the object exists in the image. The determination module may be also configured to determine a temperature of the object based on the target region of the object in the image in response to determining that the target region of the object exists in the image.

According to yet another aspect of the present disclosure, a system for temperature measurement may be provided. The system may include an acquisition module and a determination module. The acquisition module may be configured to obtain an image of an object acquired by an imaging device. The determination module may be configured to determine whether the image satisfies a condition. The determination module may be also configured to a temperature of the object based on the image in response to determining that the image satisfies the condition.

According to yet another aspect of the present disclosure, a non-transitory computer readable medium may be provided. The non-transitory computer readable may include at least one set of instructions for temperature measurement. When executed by at least one processor of a computing device, the at least one set of instructions may cause the computing device to perform a method. The method may include obtaining an image of an object acquired by an imaging device. The method may also include determining an angle between the object and the imaging device based on the image. The angle may be defined by a reference direction and a direction that the object is facing. The method may further include determining a temperature of the object in response to determining that the angle satisfies a condition based on the image.

According to yet another aspect of the present disclosure, a non-transitory computer readable medium may be provided. The non-transitory computer readable may include at least one set of instructions for temperature measurement. When executed by at least one processor of a computing device, the at least one set of instructions may cause the computing device to perform a method. The method may include obtaining an image of an object acquired by an imaging device. The method may also include determining whether a target region of the object exists in the image. The method may further include determining a temperature of the object based on the target region of the object in the image in response to determining that the target region of the object exists in the image.

According to yet another aspect of the present disclosure, a non-transitory computer readable medium may be provided. The non-transitory computer readable may include at least one set of instructions for temperature measurement. When executed by at least one processor of a computing device, the at least one set of instructions may cause the computing device to perform a method. The method may include obtaining an image of an object acquired by an imaging device. The method may also include determining whether the image satisfies a condition. The method may further include determining a temperature of the object based on the image in response to determining that the image satisfies the condition.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a schematic flowchart illustrating an exemplary process for determining a temperature of an object according to some embodiments of the present disclosure;

FIG. 7 is a schematic flowchart illustrating an exemplary process for generating a trained machine learning model according to some embodiments of the present disclosure;

DETAILED DESCRIPTION

Figure 1:
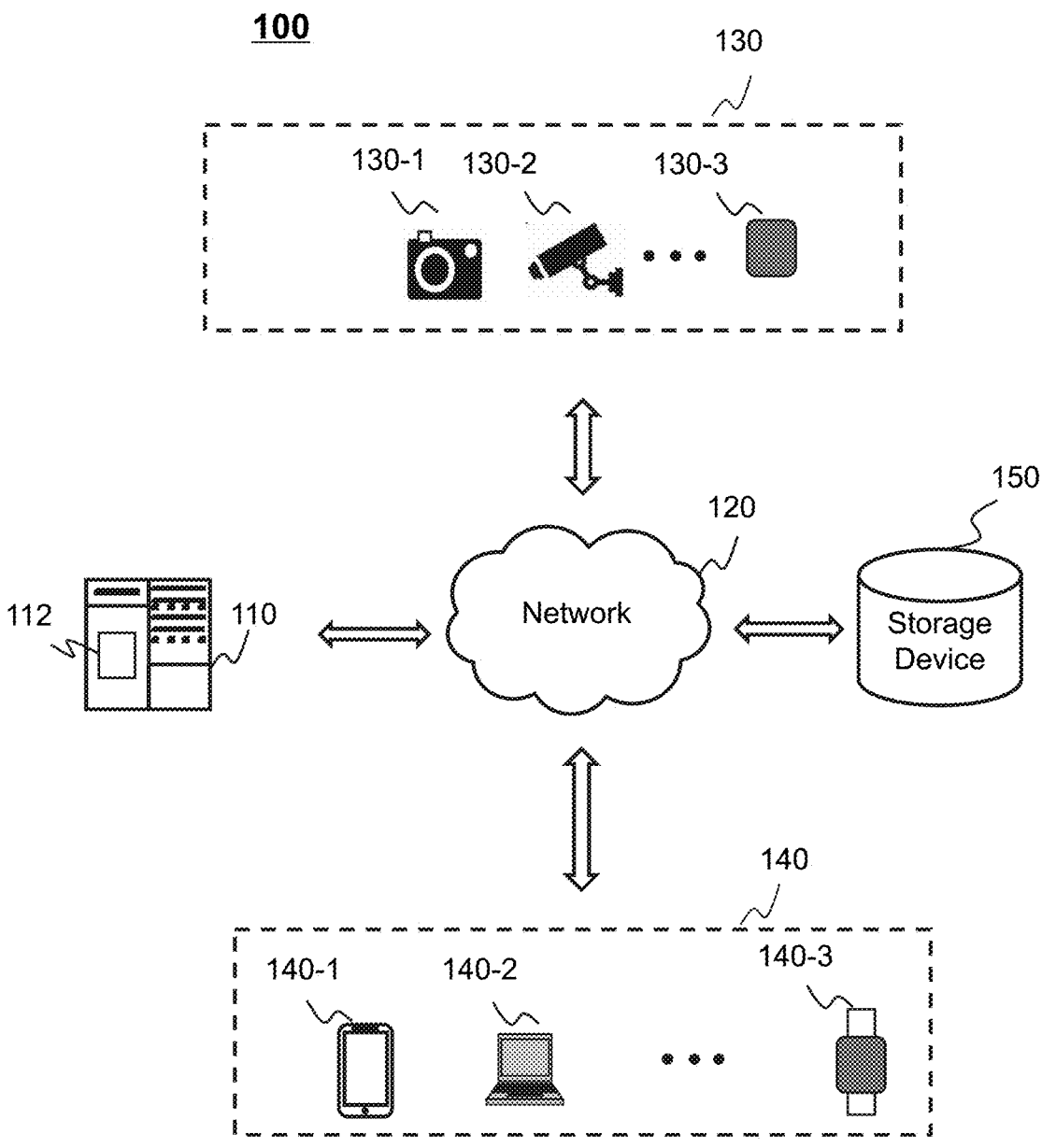
FIG. 1 is a schematic diagram illustrating an exemplary temperature measurement system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption before execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

An accurate temperature measurement is vital for, such as diagnosis of diseases. Conventionally, a temperature of an object may be determined directly based on one or more images of the object acquired by an imaging device, and each of the images of the objects may be used for the temperature measurement of the object, although a portion of the one or more images may present interference areas (e.g., an ear of a human body) for the temperature measurement, which may decrease the efficiency and accuracy of temperature measurement. Further, after determining that a temperature of an object exceeds a threshold, temperature information of all points of each image of the object may be used to determine the temperature of the object, which increases the computing amount and costs more computing resources, thereby further decreasing the efficiency and accuracy of temperature measurement. In some occasions, when an object is moving, different images of an object acquiring by an imaging device may include different parts of the object. If temperatures of different parts of the object are different, the temperature of the object acquired based on the images including different parts of the object has a limited accuracy or is inaccurate. Merely by way of example, temperatures of different parts of a human being are different. For example, the temperature of ear area of a human being is usually higher than the temperature of the facial area or the forehead area. If the temperature of the face area or forehead area of a human being is used as the temperature of the human being, some images acquired by the imaging device may include less or even no the facial area or forehead area during walking, causing the temperature of the human being determined based on these images with a limited accuracy or inaccuracy.

An aspect of the present disclosure relates to systems and methods for temperature measurement. The system may obtain an image of an object acquired by an imaging device. The system may also determine an angle between the object and the imaging device when the image is acquired by the imaging device based on the image. The angle may be defined by a reference direction and a direction that the object facing. The system may further determine the temperature of the object based on the image in response to determining that the angle satisfies a condition. The angle satisfying the condition may be such that a target region (e.g., the facial area, the forehead area of the human body) that are used to detect temperature of the object may be represented in the image. Compared with the conventional temperature measurement approach which does not involve determine whether the images are suitable for determining the temperature of the object, systems and methods of the present disclosure may determine the temperature of the object only using the images that satisfies a condition (e.g., an angle between the object and the imaging device when the image is acquired by the imaging device satisfies a condition, or a target region of the object exists in the image, etc.). In this way, images that do not satisfy the conditions may be filtered out and not be used to determine the temperature of the object, thereby improving the efficiency and accuracy of the temperature measurement of the object.

Moreover, in some embodiments, the determining of the angle between the object and the imaging device may be implemented based on a trained machine learning model (e.g., an angle detection model). The utilization of the trained machine learning model may further improve the accuracy and/or efficiency of the temperature measurement.

FIG. 1 is a schematic diagram illustrating an exemplary temperature measurement system according to some embodiments of the present disclosure. In some embodiments, the temperature measurement system 100 may be applied in various application scenarios, for example, body temperature measurement of a person, etc. As shown, the temperature measurement system 100 may include a server 110, a network 120, an imaging device 130, a terminal device 140, and a storage device 150.

The server 110 may be a single server or a server group. The server group may be centralized or distributed (e.g., the server 110 may be a distributed system). In some embodiments, the server 110 may be local or remote. For example, the server 110 may access information and/or data stored in the imaging device 130, the terminal device 140, and/or the storage device 150 via the network 120. As another example, the server 110 may be directly connected to the imaging device 130, the terminal device 140, and/or the storage device 150 to access stored information and/or data. In some embodiments, the server 110 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the server 110 may be implemented on a computing device 200 including one or more components illustrated in FIG. 2 of the present disclosure.

In some embodiments, the server 110 may include a processing device 112. The processing device 112 may process information and/or data related to temperature measurement to perform one or more functions described in the present disclosure. For example, the processing device 112 may obtain an image of an object acquired by the imaging device 130. The processing device 112 may determine an angle between the object and the imaging device 130 based on the image. Merely by way of example, the processing device 112 may determine the angle between the object and the imaging device 130 using a trained machine learning model (e.g., an angle detection model). The angle may be defined by a reference direction and a direction that the object facing. Further, the processing device 112 may determine a temperature of the object in response to determining that the angle satisfies a condition based on the image.

In some embodiments, the trained machine learning model used in the present disclosure may be updated from time to time, e.g., periodically or not, based on a sample set that is at least partially different from the original sample set from which the original trained machine learning model is determined. For instance, the trained machine learning model may be updated based on a sample set including new samples that are not in the original sample set. In some embodiments, the determination and/or updating of the trained machine learning model may be performed on a processing device, while the application of the trained machine learning model may be performed on a different processing device. In some embodiments, the determination and/or updating of the trained machine learning model may be performed on a processing device of a system different than the temperature measurement system 100 or a server different than a server including the processing device 112 on which the application of the trained machine learning model is performed. For instance, the determination and/or updating of the trained machine learning model may be performed on a first system of a vendor who provides and/or maintains such a machine learning model and/or has access to training samples used to determine and/or update the trained machine learning model, while temperature measurement based on the provided machine learning model may be performed on a second system of a client of the vendor. In some embodiments, the determination and/or updating of the trained machine learning model may be performed online in response to a request for temperature measurement. In some embodiments, the determination and/or updating of the trained machine learning model may be performed offline.

In some embodiments, the processing device 112 may include one or more processing devices (e.g., single-core processing device(s) or multi-core processor(s)).

In some embodiment, the server 110 may be unnecessary and all or part of the functions of the server 110 may be implemented by other components (e.g., the imaging device 130, the terminal device 140) of the temperature measurement system 100. For example, the processing device 112 may be integrated into the imaging device 130 or the terminal device 140 and the functions of the processing device 112 may be implemented by the imaging device 130 or the terminal device 140.

The network 120 may facilitate exchange of information and/or data for the temperature measurement system 100. In some embodiments, one or more components (e.g., the server 110, the imaging device 130, the terminal device 140, the storage device 150) of the temperature measurement system 100 may transmit information and/or data to other component(s) of the temperature measurement system 100 via the network 120. For example, the server 110 may obtain an image of an object from the imaging device 130 via the network 120. As another example, the server 110 may transmit the image and/or a temperature of the object to the terminal device 140 via the network 120.

The imaging device 130 may be and/or include any suitable device that is capable of acquiring image data. Exemplary imaging device 130 may include a camera (e.g., a digital camera, an analog camera, an IP camera (IPC), etc.), a video recorder, a scanner, a mobile phone, a tablet computing device, a wearable computing device, an infrared imaging device (e.g., a thermal imaging device), or the like. In some embodiments, the imaging device 130 may include a gun camera, a dome camera, an integrated camera, a binocular camera, a monocular camera, etc. The image data acquired by the imaging device 170 may include an image, or any data about an image, such as values of one or more pixels (or referred to as pixel values) of an image (e.g., luma, gray values, intensities, chrominance, contrast of one or more pixels of an image), RGB data, audio information, timing information, location data, etc. In some embodiments, the imaging device 130 may include a chargecoupled device (CCD), a complementary metal-oxide-semiconductor (CMOS) sensor, an N-type metal-oxide-semiconductor (NMOS), a contact image sensor (CIS), and/or any other suitable image sensor.

The terminal device 140 may be configured to receive information and/or data from the server 110, the imaging device 130, and/or the storage device 150, via the network 120. For example, the terminal device 140 may receive images from the imaging device 130. As another example, the terminal device 140 may receive the temperature of the object from the server 110. In some embodiments, the terminal device 140 may process information and/or data received from the server 110, the imaging device 130, and/or the storage device 150, via the network 120. In some embodiments, the terminal device 140 may provide a user interface via which a user may view information and/or input data and/or instructions to the temperature measurement system 100. For example, the user may view the images of the object via the user interface. As another example, the user may input an instruction associated with the temperature measurement via the user interface. In some embodiments, the terminal device 140 may include a mobile phone 140-1, a computer 140-2, a wearable device 140-3, or the like, or any combination thereof. In some embodiments, the terminal device 140 may include a display that can display information in a human-readable form, such as text, image, audio, video, graph, animation, or the like, or any combination thereof. The display of the terminal device 140 may include a cathode ray tube (CRT) display, a liquid crystal display (LCD), a light-emitting diode (LED) display, a plasma display panel (PDP), a three-dimensional (3D) display, or the like, or a combination thereof.

The storage device 150 may be configured to store data and/or instructions. The data and/or instructions may be obtained from, for example, the server 110, the imaging device 130, and/or any other component of the temperature measurement system 100. In some embodiments, the storage device 150 may store data and/or instructions that the server 110 may execute or use to perform exemplary methods described in the present disclosure. In some embodiments, the storage device 150 may include a mass storage, a removable storage, a volatile read-and-write memory, a read-only memory (ROM), or the like, or any combination thereof. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components (e.g., the server 110, the imaging device 130, the terminal device 140) of the temperature measurement system 100. One or more components of the temperature measurement system 100 may access the data or instructions stored in the storage device 150 via the network 120. In some embodiments, the storage device 150 may be directly connected to or communicate with one or more components (e.g., the server 110, the imaging device 130, the terminal device 140) of the temperature measurement system 100. In some embodiments, the storage device 150 may be part of other components of the temperature measurement system 100, such as the server 110, the imaging device 130, or the terminal device 140.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 2:
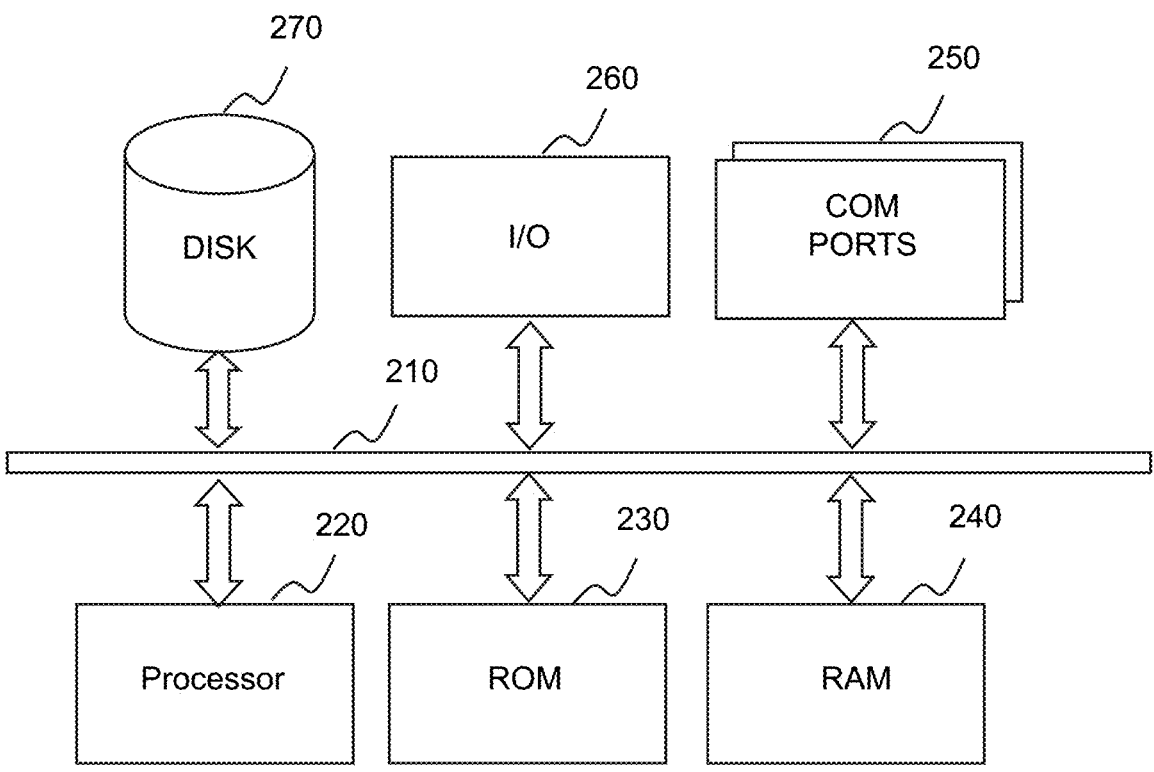
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. In some embodiments, the server 110 may be implemented on the computing device 200. For example, the processing device 112 may be implemented on the computing device 200 and configured to perform functions of the processing device 112 disclosed in this disclosure.

The computing device 200 may be used to implement any component of the temperature measurement system 100 as described herein. For example, the processing device 112 may be implemented on the computing device 200, via its hardware, software program, firmware, or a combination thereof. Although only one such computer is shown, for convenience, the computer functions relating to object measurement as described herein may be implemented in a distributed fashion on a number of similar platforms to distribute the processing load.

The computing device 200, for example, may include COM ports 250 connected to and from a network connected thereto to facilitate data communications. The computing device 200 may also include a processor (e.g., a processor 220), in the form of one or more processors (e.g., logic circuits), for executing program instructions. For example, the processor 220 may include interface circuits and processing circuits therein. The interface circuits may be configured to receive electronic signals from a bus 210, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus 210.

The computing device 200 may further include program storage and data storage of different forms including, for example, a disk 270, a read-only memory (ROM) 230, or a random-access memory (RAM) 240, for storing various data files to be processed and/or transmitted by the computing device 200. The computing device 200 may also include program instructions stored in the ROM 230, RAM 240, and/or another type of non-transitory storage medium to be executed by the processor 220. The methods and/or processes of the present disclosure may be implemented as the program instructions. The computing device 200 may also include an I/O component 260, supporting input/output between the computing device 200 and other components. The computing device 200 may also receive programming and data via network communications.

Merely for illustration, only one processor is illustrated in FIG. 2. Multiple processors 220 are also contemplated; thus, operations and/or method steps performed by one processor 220 as described in the present disclosure may also be jointly or separately performed by the multiple processors. For example, if in the present disclosure the processor 220 of the computing device 200 executes both step A and step B, it should be understood that step A and step B may also be performed by two different processors 220 jointly or separately in the computing device 200 (e.g., a first processor executes step A and a second processor executes step B, or the first and second processors jointly execute steps A and B).

Figure 3:
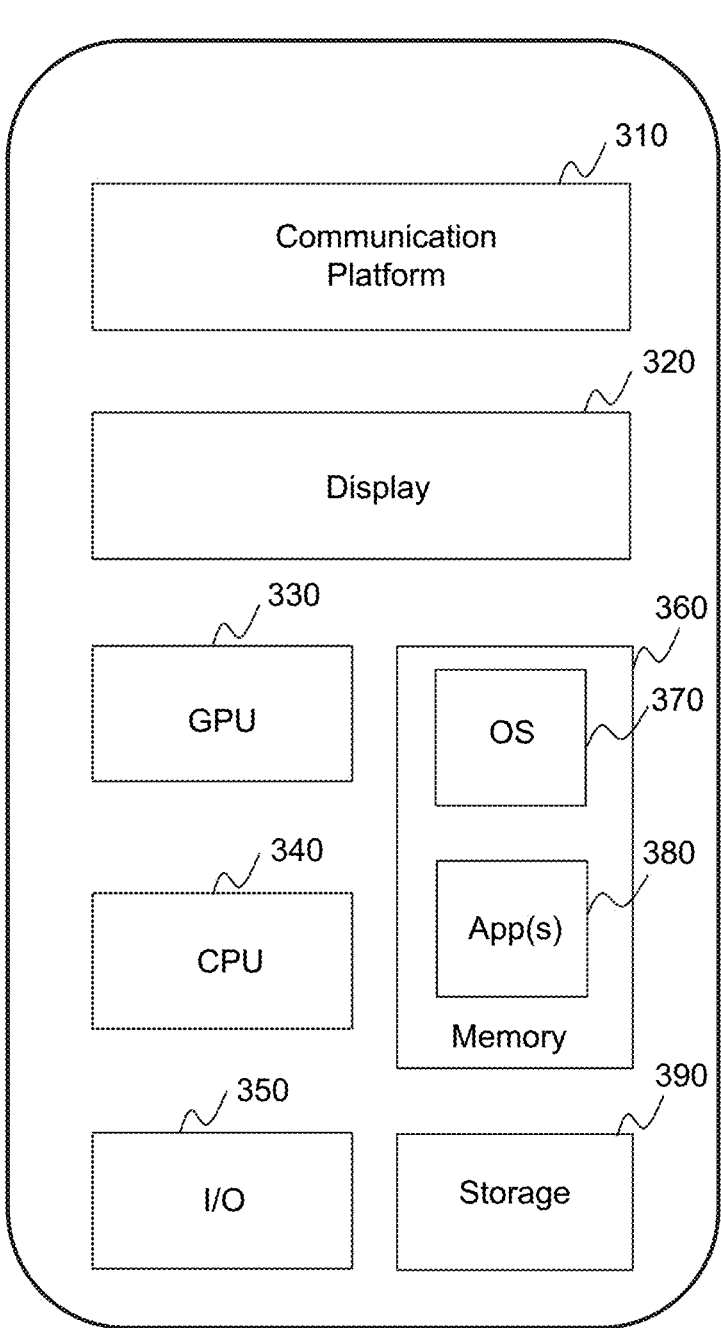
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal device 140 may be implemented on the mobile device 300 shown in FIG. 3.

As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, an operating system 370 (e.g., iOS™, Android™, Windows Phone™) and one or more applications (Apps) 380 may be loaded into the memory 360 from the storage 390 in order to be executed by the CPU 340. The applications 380 may include a browser or any other suitable mobile apps for receiving and rendering information relating to measurement or other information from the processing device 112. User interactions may be achieved via the I/O 350 and provided to the processing device 112 and/or other components of the temperature measurement system 100 via the network 120.

Figure 4A:
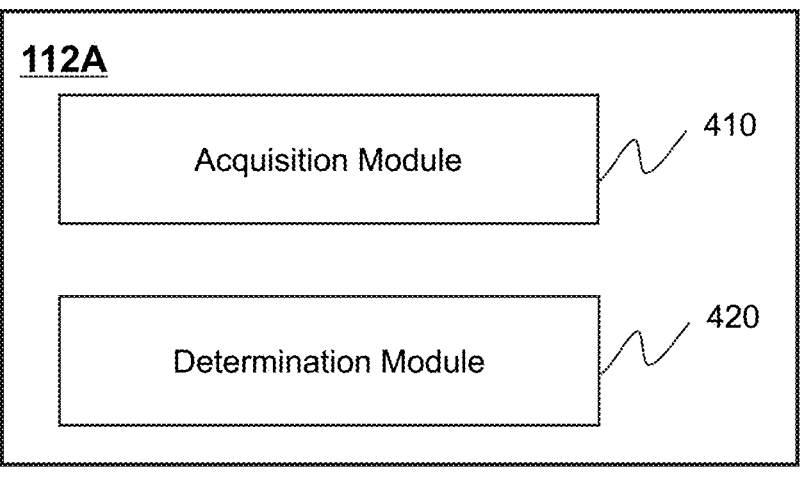
FIG. 4A is a block diagram illustrating exemplary processing device 112A for temperature measurement according to some embodiments of the present disclosure.
Figure 4B:
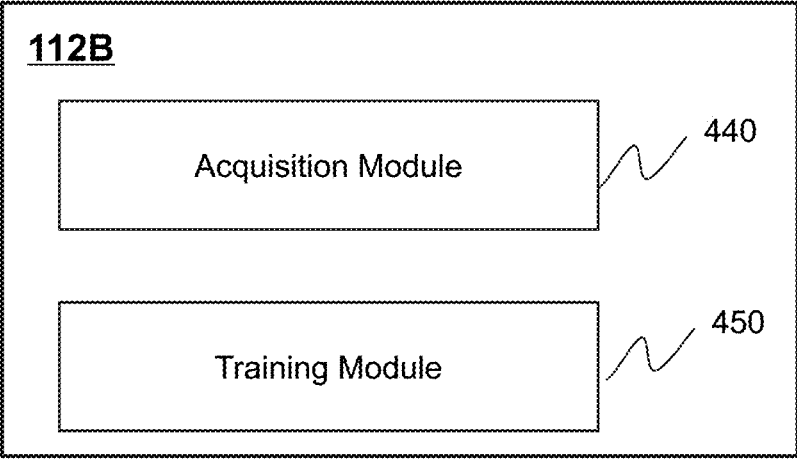
FIG. 4B is a block diagram illustrating exemplary processing device 112B for training an angle detection model according to some embodiments of the present disclosure.

FIG. 4A is a block diagram illustrating exemplary processing device 112A for temperature measurement according to some embodiments of the present disclosure. FIG. 4B is a block diagram illustrating exemplary processing device 112B for training an angle detection model according to some embodiments of the present disclosure. The processing devices 112A and 112B may be exemplary processing devices 112 as described in connection with FIG. 1. In some embodiments, the processing device 112A may be configured to apply one or more machine learning models in determining a temperature of an object. The processing device 140B may be configured to generate the one or more machine learning models. In some embodiments, the processing devices 112A and 112B may be respectively implemented on a processing unit (e.g., a processor 220 illustrated in FIG. 2 or a CPU 330 as illustrated in FIG. 3). Merely by way of example, the processing devices 112A may be implemented on a CPU 330 of a terminal device, and the processing device 112B may be implemented on a computing device 200. Alternatively, the processing devices 112A and 112B may be implemented on a same computing device 200 or a same CPU 330. For example, the processing devices 112A and 112B may be implemented on a same computing device 200.

As shown in FIG. 4A, the processing device 112A may include an acquisition module 410 and a determination module 420.

The acquisition module 410 may be configured to obtain information relating to the temperature measurement system 100. For example, the acquisition module 410 may obtain an image of an object acquired by an imaging device. As used herein, the object may be a biological object (e.g., a human being, an animal, or a portion thereof), or a non-biological object (e.g., a vehicle, a building). For example, the object may include a body of a personal or a portion thereof (e.g., the head, the face, etc.). In some embodiments, the image may include a thermal infrared image, a visible image, or any other type of images. In some embodiments, the image may be a two-dimensional (2D) image, a three-dimensional (3D) image, a four-dimensional (4D), or any other type of image. More descriptions regarding the obtaining of the image of the object may be found elsewhere in the present disclosure. See, e.g., operation 510 in FIG. 5, and relevant descriptions thereof.

The determination module 420 may be configured to determine an angle between the object and the imaging device when the image is acquired by the imaging device based on the image, and determine whether the angle between the object and the imaging device satisfies a condition. In response to a determination that the angle between the object and the imaging device when the imaging device acquires the image satisfies the condition, the determination module 420 may determine a temperature of the object based on the image. More descriptions regarding the determination of the angle between the object and the imaging device and the determination of the temperature of the object based on the image may be found elsewhere in the present disclosure. See, e.g., operations 503-507 in FIG. 5, and relevant descriptions thereof.

In some embodiments, the determination module 420 may be configured to determine whether a target region of the object exists in the image. In response to a determination that the target region of the object exists in the image, the determination module 420 may determine a temperature of the object based on the target region of the object in the image. More descriptions regarding determining whether a target region of the object exists in the image and the determination of the temperature of the object based on the target region of the object in the image may be found elsewhere in the present disclosure. See, e.g., operations 803 and 805 in FIG. 8, and relevant descriptions thereof.

In some embodiments, the determination module 420 may be configured to determine whether the image satisfies a condition. In response to a determination that the image satisfies a condition, the determination module 420 may determine a temperature of the object based on the image. More descriptions regarding determining whether the image satisfies a condition and the determination of the temperature of the object based on the image may be found elsewhere in the present disclosure. See, e.g., operations 903 and 905 in FIG. 9, and relevant descriptions thereof.

As shown in FIG. 4B, the processing device 112B may include an acquisition module 440 and a training module 450.

The acquisition module 440 may be configured to obtain data used to generate a trained machine learning model. For example, the acquisition module 440 may be configured to obtain a plurality of training samples each of which includes a sample image of a sample object acquired by a sample imaging device. Each of at least a portion of sample images may be labeled with a sample angle between the sample object corresponding to the sample image and the sample imaging device. More descriptions regarding the acquisition of the training samples may be found elsewhere in the present disclosure. See, e.g., operation 701 in FIG. 7, and relevant descriptions thereof.

The training module 450 may be configured to generate the trained machine learning model by training a preliminary machine learning model using the plurality of training samples. In some embodiments, the trained machine learning model may be generated according to a machine learning algorithm by training the preliminary machine learning model. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the one or more machine learning models may be a supervised learning algorithm, a semi-supervised learning algorithm, an unsupervised learning algorithm, or the like. More descriptions regarding the generation of the trained machine learning model may be found elsewhere in the present disclosure. See, e.g., operation 703 in FIG. 7, and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 112A as described in FIG. 4A and/or the processing device 112B as described in FIG. 4B may share two or more of the modules, and any one of the modules may be divided into two or more units. For instance, the processing device 112A as described in FIG. 4A and the processing device 112B as described in FIG. 4B may share a same acquisition module; that is, the acquisition module 410 and the acquisition module 440 are a same module. In some embodiments, the processing device 112A as described in FIG. 4A and/or the processing device 112B as described in FIG. 4B may include one or more additional modules, such as a storage module (not shown) for storing data. In some embodiments, the processing device 112A as described in FIG. 4A and the processing device 112B as described in FIG. 4B may be integrated into one processing device 112.

Figure 5:
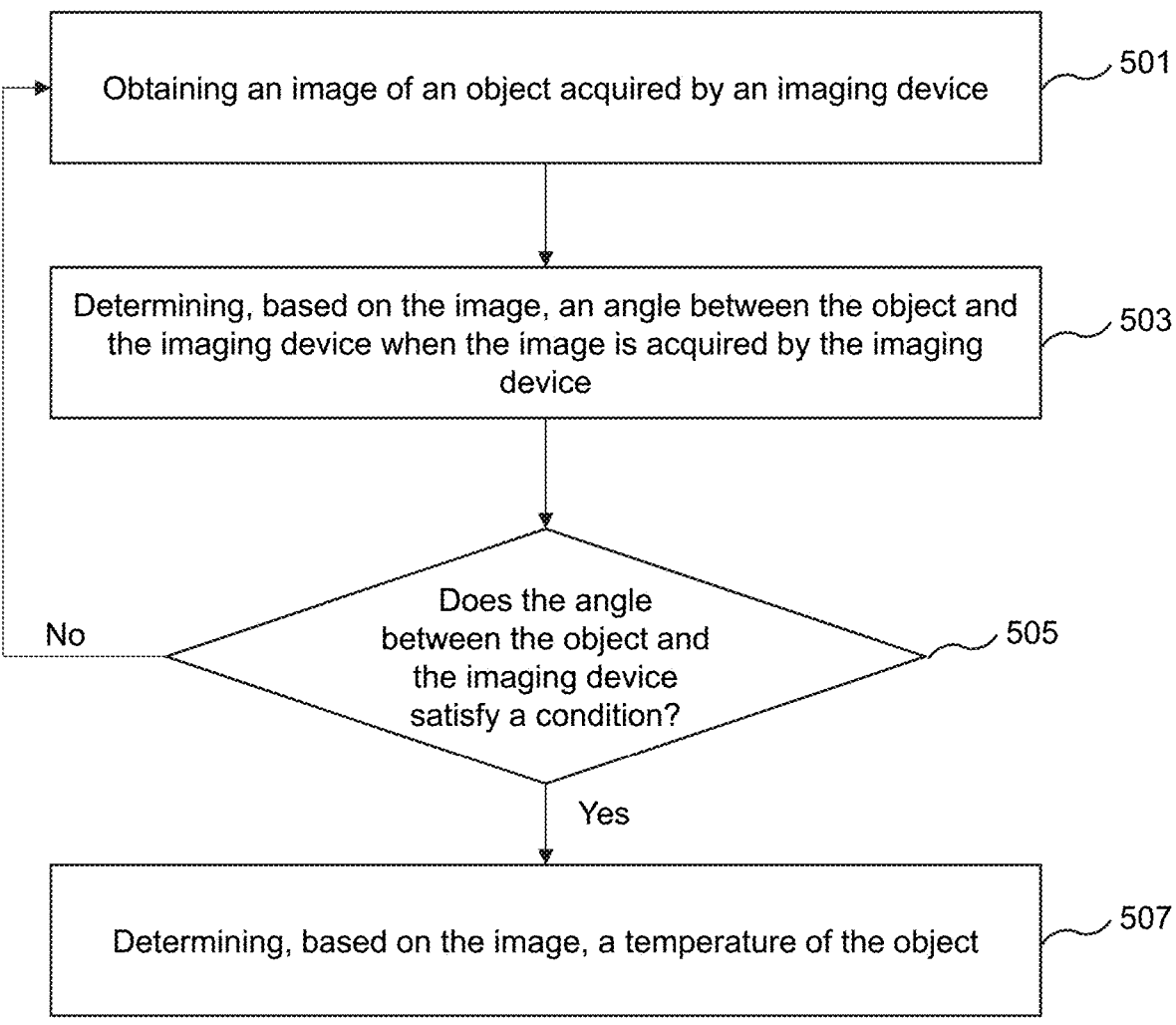
FIG. 5 is a schematic flowchart illustrating an exemplary process for determining a temperature of an object according to some embodiments of the present disclosure.

FIG. 5 is a schematic flowchart illustrating an exemplary process for determining a temperature of an object according to some embodiments of the present disclosure. In some embodiments, a process 500 may be implemented as a set of instructions (e.g., an application) stored in the storage device 150, ROM 230 or RAM 240, or storage 390. The processing device 112A, the processor 220, and/or the CPU 330 may execute the set of instructions, and when executing the instructions, the processing device 112A, the processor 220, and/or the CPU 330 may be configured to perform the process 500. The operations of the illustrated process presented below are intended to be illustrative. In some embodiments, the process 500 may be accomplished with one or more additional operations not described and/or without one or more of the operations discussed. Additionally, the order in which the operations of the process 500 illustrated in FIG. 5 and described below is not intended to be limiting.

In 501, the processing device 112A (e.g., the acquisition module 410) may obtain an image of an object acquired by an imaging device.

As used herein, the object may be a biological object (e.g., a human being, an animal, or a portion thereof), or a non-biological object (e.g., a vehicle, a building). For example, the object may include a body of a personal or a portion thereof (e.g., the head, the face, etc.). In some embodiments, the image may include a thermal infrared image, a visible image, or any other type of images. In some embodiments, the image may be a two-dimensional (2D) image, a three-dimensional (3D) image, a four-dimensional (4D), or any other type of image. The image may be stored in any image format, such as a RAW format (e.g., unprocessed processed image data), a tagged input file format (TIFF), a joint photographic experts group format (JPEG), a graphics interchange format (GIF), or a bitmap format (BMP), or the like, or the combination thereof.

In some embodiments, the imaging device may include any type of device that is capable of acquiring image data as described elsewhere in this disclosure (e.g., FIG. 1 and the relevant descriptions), such as a camera (e.g., a digital camera, an analog camera, an IP camera (IPC), etc.), a video recorder, a scanner, a mobile phone, a tablet computing device, a wearable computing device, an infrared imaging device, or the like. In some embodiments, the imaging device may automatically capture the image of the object when or after the object enters a detecting region of the imaging device. In some embodiments, the processing device 112A may obtain the image from the imaging device. Alternatively, the image may be acquired by the imaging device and stored in a storage device (e.g., the storage device 150, the storage 390, or an external source). The processing device 112A may retrieve the image from the storage device.

In 503, the processing device 112A (e.g., the determination module 420) may determine, based on the image, an angle between the object and the imaging device when the image is acquired by the imaging device.

The angle between the object and the imaging device may be defined by a reference direction and a direction the object facing. The angle between the object and the imaging device may be an angle between the reference direction of and the direction the object facing. As use herein, a direction that an object is facing refers to a direction substantially perpendicular to a target region or a target surface including the target region of the object and pointing outward. The target region of the object may be a region of interest of the object for temperature detection (or measurement). In other words, the temperature of the object may be detected from the target region of the object. For example, the object may include a human body or the head of the human body, and the target region may include the facial area or the forehead area of the human body. As another example, the object may include a back surface and a front surface, the front surface may be the target surface, and the direction that the object is facing may be from the back surface of the object pointing to the front surface of the object. Merely by way of example, if a front surface of an object is facial area, the direction that the object is facing refers to a direction from the back portion of the head of the object to the front portion (referred to as a face portion) of the head of the object.

In some embodiments, the reference direction may be related to a position relationship between the imaging device and the object. In some embodiments, the reference direction may be a direction of an optic axis of the imaging device pointing from a side of the imaging device facing the object to the imaging device. For example, if the object is located at the optic axis of the imaging device, the reference direction may be a direction of the optic axis of the imaging device pointing from a side of the imaging device facing the object to the imaging device. In some embodiments, the reference direction may be a direction of a reference line horizontally connecting the imaging device and the object, and the direction of the reference line may point from the object to the imaging device. For example, the reference line may be a horizontal line that passes through the geometric center point of the object and intersect a vertical line passing through the geometric center point of the imaging device. The range of the angle between the object and the imaging device may be in a range from 0 degree to 180 degrees.

In some embodiments, if the reference direction is the direction of the optic axis of the imaging device pointing from the side of the imaging device facing the object to the imaging device, and the reference direction and the direction of the object facing are opposite, the angle between the object and the imaging device may be 180 degrees, that means the object is back to the imaging device and the target region of the object may be not represented in the image; if the reference direction and the direction of the object facing are the same, the angle between the object and the imaging device may be 0 degree, that means the object is facing the imaging device and the whole of the target region of the object may be represented in the image; if the angle between the object and the imaging device exceeds 0 degree and smaller than 90 degrees, most of the target region of the object may be represented in the image; if the angle between the object and the imaging device exceeds 90 degree and smaller than 180 degrees, a small part of the target region of the object may be represented in the image.

In some embodiments, the processing device 112A may determine the angle between the object and the imaging device based on the image using an angle detection model that associated with a plurality of reference images of reference objects. A reference image of a reference object may be acquired by a reference imaging device and correspond to a reference angle between the reference object and the reference imaging device. The reference angle between the reference object and the reference imaging device may be an angle between the reference object and the reference imaging device when the reference image is acquired. Similar to the image, a reference image may be of any type and stored in any image format. A reference image may be an image of a biological object, or an image of a non-biological object. Different reference images may have the same image type (or format) or different image types (or formats). The image and the plurality of reference images may be images of a same type of object, for example, both of the image and the plurality of reference images may be images of human beings. In some embodiments, the reference imaging device may be a same type of imaging device as the imaging device as described in connection with operation 501. In some embodiments, the reference imaging device may be the same imaging device as the imaging device as described in connection with operation 501.

In some embodiments, the angle detection model may include a trained machine learning model. In some embodiments, the trained machine learning model may include a deep learning model, such as a deep neural network (DNN) model, a convolutional neural network (CNN) model, a recurrent neural network (RNN) model, a feature pyramid network (FPN) model, etc. Exemplary CNN models may include a V-Net model, a U-Net model, a Link-Net model, or the like, or any combination thereof. In some embodiments, the trained machine learning model may include a regression model, such as a linear regression model, a K-nearest neighbor model, etc.

In some embodiments, the trained machine learning model may be obtained by training a preliminary machine learning model using the plurality of reference images of reference objects and the reference angles corresponding to the plurality of reference images. In the training of the preliminary machine learning model, the plurality of reference images of reference objects may serve as inputs of the preliminary machine learning model and the reference angles corresponding to the plurality of reference images may serve as desired outputs. The preliminary machine learning model may be trained to decrease a deviation between an actual output generated based on an input (i.e., a reference image) and a desired output (i.e., a reference angle) corresponding to the input. The preliminary machine learning model may be trained to learn a corresponding relationship between a specific image (e.g., the image as described in operation 501) of a specific object (or image features of the specific image) and an angle between a specific imaging device (e.g., the imaging device as described in operation 501) and the specific object (e.g., the object as described in operation 501) when the specific image is acquired by the specific imaging device. The trained machine learning model may be configured to deter- mine the angle between the specific imaging device and the specific object based on the corresponding relationship between the specific image of the specific object (or image features of the image) and the angle between the specific imaging device and the specific object when the specific image is acquired. The specific image may be any image acquired by an imaging device that is the same as or different from the imaging device acquiring the image in 501 or the reference imaging device acquiring the reference images. In some embodiments, the trained machine learning model may be generated according to a machine learning algorithm as described elsewhere in this disclosure (e.g., FIG. 4 and the relevant descriptions). More descriptions for the generation of the trained machine learning model may be found else- where in the present disclosure (e.g., FIG. 7 and the descrip- tions thereof).

In some embodiments, the processing device 112A may obtain the trained machine learning model from one or more components of the temperature measurement system 100 (e.g., the storage device 150, the terminal device 140, the imaging device 130, etc.) or an external source via a network (e.g., the network 120). For example, the trained machine learning model may be previously trained by a computing device (e.g., the processing device 112B), and stored in a storage device (e.g., the storage device 150) of the tempera- ture measurement system 100. The processing device 112A may access the storage device and retrieve the trained machine learning model.

In some embodiments, the image may be inputted into the trained machine learning model, and the trained machine learning model may directly output the angle between the imaging device and the object. In some embodiments, the image may be inputted into the trained machine learning model, and the trained machine learning model may output information relating to the angle. For example, the trained machine learning model may output the direction informa- tion that the object facing, and the processing device 112A may determine the angle based on the optic axis of the imaging device in the direction away from the object and the direction information that the object facing. In some embodiments, image features extracted from the image may be inputted into the trained machine learning model, and the trained machine learning model may directly output the angle between the imaging device and the object based on the image features.

In some embodiments, the angle detection model may include a first portion configured to perform a feature extraction (such as extraction of lines, edges and ridges, or localization of interest points), and a second portion con- figured to provide a corresponding relationship between each of the plurality of reference images of reference objects and the reference angle between the reference object and the reference imaging device. In some embodiments, the angle detection model may include a third portion configured to determine at least one target reference image from the plurality of reference images that matches the image and determine the angle between the imaging device and the object based on the at least one reference angle correspond- ing to the at least one target reference image that matches the image.

In some embodiments, the first portion of the angle detection model may be configured to extract image features associated with the angle (e.g., angle features) from the image and/or reference image features associated with the reference angle corresponding to the reference image (e.g., reference angle features) from each of the plurality of reference images. Exemplary image features may include angle features (e.g., corner features), color features, shape features, spatial relationship feature, etc. For example, the first portion of the angle detection model may identify at least one feature point associated with the object from the image. The at least one feature point may include one or more points (pixels) of a specific part (e.g., the forehead, eyes, the nose, the mouth, ears) of the object in the image. The identification of the at least one feature point associated with the object may be further used to compare with the feature points in each reference image to determine whether the feature points of the reference image match the feature points of the image, and further determine the angle between the object and the imaging device based on the comparison.

In some embodiments, the first portion of the angle detection model may include applying a feature extraction algorithm. Exemplary feature extraction algorithms may include a scale invariant feature transform (SIFT) algorithm, an average amplitude difference function (AMDF) algo- rithm, a histogram of gradient (HOG) algorithm, a speeded up robust features (SURF) algorithm, a local binary pattern (LBP) algorithm, etc. In some embodiments, the angle features and the reference angle features may include fea- tures associated with corner points of the image and each of the plurality of reference image. The first portion of the angle detection model may be configured to determine corner points of the image and each of the plurality of reference images using a corner detection algorithm. Exem- plary corner detection algorithms may include a Moravec corner detection algorithm, a Harris corner detection algo- rithm, a Susan corner detection algorithm, etc. In some embodiments, the first portion of the angle detection model may include applying a trained machine learning for feature extraction, e.g., a trained CNN model.

In some embodiments, the second portion may represent the corresponding relationship between each of the plurality of reference images of reference objects (or reference image features, or a vector including the reference image features) and the reference angle between the reference object and the reference imaging device as a table. For example, the table may include multiple reference images and multiple refer- ence angles. Each of the multiple reference images may correspond to one of the multiple reference angles. The second portion may be stored in a database. In some embodiments, the second portion may represent the corre- sponding relationship between each of the plurality of reference images of reference objects and the reference angle between the reference object and the reference imag- ing device as a function. The function may be related to one or more reference image features and the reference angle. For example, the reference angle may be the dependent variable of the function and the one or more reference image features are the independent variables of the function.

The third portion of the angle detection model may be configured to determine at least one target reference image from the plurality of reference images that matches the image. The at least one target reference image that matches the image may be at least one of the plurality of reference images whose reference angle features match the angle features of the image. The reference angle features of the reference image may match the angle features of the image if a similarity between reference angle features of a reference image and the angle features of the image exceeds a threshold, such as 90%, 95%, 99%, etc.

Merely by way of example, the third portion of the angle detection model may compare reference angle features of each of the plurality of reference images with the angle features of the image provided by the first portion of the angle detection model. The third portion of the angle detection model may determine the at least one target reference image based on the comparison.

For example, the third portion of the angle detection model may determine a similarity between reference angle features of each of the plurality of reference images and the angle features of the image. The third portion of the angle detection model may determine the at least one target reference image based on the similarity between reference angle features of each of the plurality of reference images and the angle features of the image. The third portion of the angle detection model may determine the at least one target reference image based on one or more reference images whose similarities exceed a threshold, such as 90%, 95%, 99%, etc. For example, a reference image with a maximum similarity among the one or more reference images whose similarities exceed the threshold may be designated as the target reference image. As another example, the one or more reference images whose similarities exceed the threshold may be designated as one or more target reference images. In some embodiments, the third portion of the angle detection model may determine a similarity between reference angle features of a reference image and the angle features of the image using a similarity algorithm. The similarity algorithm may include but be not limited to a Euclidean distance algorithm, a Manhattan distance algorithm, a Minkowski distance algorithm, a cosine similarity algorithm, a Jaccard similarity algorithm, a Pearson correlation algorithm, or the like, or any combination thereof.

The third portion of the angle detection model may be configured to determine at least one target reference angle corresponding to the at least one target reference image based on the corresponding relationship between each of the plurality of reference images of reference objects and the reference angle between the reference object and the reference imaging device and the at least one target reference image. For example, the third portion of the angle detection model may retrieve the at least one target reference angle corresponding to the at least one target reference images from the table that includes the corresponding relationship between each of the plurality of reference images of reference objects and the reference angle between the reference object and the reference imaging device. As another example, the third portion of the angle detection model may be configured to determine the at least one target reference angle by inputting the reference image features of the at least one target reference images into the function related to one or more reference image features and the reference angle.

The third portion of the angle detection model may output the at least one target reference angle corresponding to the at least one target reference image in the table and/or information relating to the at least one target reference angle (e.g., the similarity between reference angle features of each target reference image and the angle features of the image).

In some embodiments, the processing device 112A may determine the angle between the object and the imaging device based on the at least one target reference angle corresponding to the at least one target reference image. In some embodiments, the processing device 112A may determine an average angle or a median angle of the at least one target reference angle as the angle between the object and the imaging device. In some embodiments, the processing device 112A may determine a final target reference angle from the at least one target reference angle as the angle between the object and the imaging device based on a position relationship between the reference imaging device and the reference object in each target reference image and a position relationship between the imaging device and the object in the image. For example, the position relationship between the reference imaging device and the reference object in each target reference image may include a distance between the reference object and the reference imaging device, and the position relationship between the imaging device and the object in the image may include a distance between the object and the imaging device, the processing device 112A may determine a specific target reference angle corresponding to a specific target reference image as the angle between the object and the imaging device if the distance between the reference object represented in the specific target reference image and the reference imaging device is most close to the distance between the object and the imaging device. In some embodiments, the processing device 112A may determine a final target reference angle from the at least one target reference angle as the angle between the object and the imaging device based on personalized characteristics of the reference object represented in each target reference image and personalized characteristics of the object in the image. The personalized characteristics may include the age, the gender, the size, etc.

In some embodiments, the plurality of reference images of reference objects and the reference angles corresponding to the plurality of reference images may be stored in a database. Each reference image may be labeled with the reference angle corresponding to the reference image. The processing device 112A or the angle detection model may obtain the plurality of reference images and the reference angles from database. The processing device 112A or the angle detection model may compare each reference image with the image. For example, the processing device 112A or the angle detection model may compare reference angle features of each reference image with the angle features of the image. The processing device 112A or the angle detection model may determine the angle of the image based on the comparison. The reference angle corresponding to the reference image may be determined as the angle of the image if the discrepancy between the reference image and the image does not exceed a certain threshold.

In 505, the processing device 112A (e.g., the determination module 420) may determine whether the angle between the object and the imaging device satisfies a condition.

In some embodiments, the condition may include an angle threshold. Whether the angle between the object and the imaging device satisfies the condition may include whether the angle between the object and the imaging device is smaller than or equal to the angle threshold. If the angle between the object and the imaging device is smaller than or equal to the angle threshold, the angle between the object and the imaging device may satisfy the condition. In some embodiments, the condition may include an angle range. Whether the angle between the object and the imaging device satisfies the condition may include whether the angle between the object and the imaging device is in the angle range. If the angle between the object and the imaging device is in the angle range, the angle between the object and the imaging device may satisfy the condition.

In some embodiments, the angle threshold and/or the angel range may be determined according to, such as a type of the object, a target region of the object used to determine a temperature of the object, etc. For example, different angle thresholds may need to be determined for different types of objects. As another example, different angle thresholds may need to be determined for different target regions of a same type of object. In some embodiments, the angle threshold and/or the angel range may be set manually by a user according to an experience value or a default setting of the temperature measurement system 100, or determined by the processing device 112A according to an actual need.

In some embodiments, if the reference direction is the direction of the optic axis of the imaging device pointing from a side of the imaging device facing the object to the imaging device, the angle threshold may be equal to 15 degrees, 20 degrees, 30 degrees, 60 degrees, 90 degrees, etc., or the angle range may be from 0 to 15 degrees, or 0 to 20 degrees, or 0 to 30 degrees, or 0 to 60 degrees, or 0 to 90 degrees, etc.

In some embodiments, if the reference direction is the direction of a reference line horizontally connecting the imaging device and the object and pointing from the object to the imaging device, the angle threshold may be related to the angle between the optic axis of the imaging device and the reference direction. For example, if the angle between the optic axis of the imaging device and the reference direction is equal to $\alpha$, the angle threshold may be equal to $(\alpha+15)$ degrees, $(\alpha+20)$ degrees, $(\alpha+30)$ degrees, $(\alpha+60)$ degrees, $(\alpha+90)$ degrees, etc.

In response to a determination that the angle does not satisfy the condition, the processing device 112A may proceed to perform operation 501 and operation 503. The processing device 112A may obtain an additional image (or a next image) of the object acquired by the imaging device, and assess the angle between the object and the imaging device when the imaging device acquires the additional image.

In response to a determination that the angle between the object and the imaging device when the imaging device acquires the image satisfies the condition, the processing device 112A may proceed to perform operation 507.

In 507, the processing device 112A (e.g., determination module 420) may determine, based on the image, a temperature of the object.

In some embodiments, a target region of the object may be identified from the image. A temperature of the target region may be an approximate representation of the temperature of the object. For example, for a human being, the target region may include at least one of a facial area or a forehead area.

In some embodiments, the target region may be enclosed by a bounding box, that is, the bounding box may represent the target region. The target region may be identified using the bounding box. The bounding box may be 2-dimensional or 3-dimensional. For example, if the image is a 2-dimensional image, the bounding box may have the shape of a square, a rectangle, a triangle, a polygon, a circle, an ellipse, an irregular shape, or the like. As another example, if the image is a 3-dimensional image, the bounding box may have the shape of a cube.

In some embodiments, the target region may be identified from the image manually by a user (e.g., a doctor, an imaging specialist, a technician) by, for example, drawing the bounding box on the image displayed on a user interface.

Alternatively, the target region may be identified by the processing device 112A automatically according to an image analysis algorithm (e.g., an image segmentation algorithm). For example, the processing device 112A may perform image segmentation on the image using an image segmentation algorithm to generate the target region. Exemplary image segmentation algorithm may include a threshold-based segmentation algorithm, a compression-based algorithm, an edge detection algorithm, a machine learning-based segmentation algorithm, or the like, or any combination thereof.

In some embodiments, the bounding box may be defined by at least one of one or more geometric parameters and position parameters. Exemplary geometric parameters may include a shape, a size, of the bounding box, etc. Exemplary position parameters may include coordinates of the center point of the bounding box, coordinates of edge points, coordinates of vertexes of the bounding box, etc. For example, if the bounding box is a rectangle box, the geometric parameters of the bounding box may include a length and a width of the rectangle box, and the position parameters of the bounding box may include coordinates of the center point and coordinates of vertexes of the rectangle box. As another example, if the bounding box is a circular box, the geometric parameters of the bounding box may include a radius of the circular box, and the position parameters of the bounding box may include coordinates of the center point of the circular box.

The processing device 112A may determine the geometric parameter(s) and position parameter(s) based on the image, and then identity the target region from the image based on at least one of the geometric parameter(s) and position parameter(s). The processing device 112A may represent the target region using the bounding box with the geometric parameter(s) and position parameter(s). In some embodiments, the geometric parameter(s) and position parameter(s) may be determined automatically by the processing device 112A and/or manually by a user through a terminal device. For example, the geometric parameter(s) and position parameter(s) may be determined inputting by a user on a user interface.

In some embodiments, one or more temperature measurement modes each of which corresponds a type of target region may be previously set by a user or the processing device 112A. For example, the temperature measurement mode(s) may include a facial measurement mode in which the target region is the facial area, a forehead measurement mode in which the target region is the forehead area, an eyebrows center measurement mode in which the target region is the forehead area and eyes region, etc. A user may select the temperature measurement mode by inputting or clicking the corresponding temperature measurement mode.

In some embodiments, the processing device 112A may determine the temperature of the object based on temperature information of the target region. For example, the processing device 112A may determine the maximum temperature of the target region as the temperature of the object. As another example, the processing device 112A may determine an average of temperatures of a plurality of pixel points or voxel points in the target region as the temperature of the object.

In some embodiments, the image may include temperature information of the object. For example, the image may be a thermal infrared image including temperature information acquired by the imaging device including a thermal infrared imaging apparatus. The processing device 112A may directly determine the temperature of the object based on the temperature information of the target region in the image.

In some embodiments, the image does not include temperature information of the object. For example, the image may be a visible image without temperature information of the object acquired by the imaging device (also referred to as a first imaging device) including a visible imaging apparatus. The processing device 112A may obtain a second image of the object acquired by a second imaging device including a thermal infrared imaging apparatus. The second image may include temperature information of the object. The processing device 112A may determine a position of the object (or the target region of the object) in the second image based on a position of the object (or the target region of the object) in the image (also referred to as a first image) and a transform relationship between a first coordinate system of the first imaging device and a second coordinate system of the second imaging device. The processing device 112A may further obtain the temperature information of the object based on the position of the object (or the target region) in the second image and determine the temperature of the object based on the temperature information of the object in the second image. More descriptions for determining of the temperature of the object may be found elsewhere in the present disclosure (e.g., FIG. 6 and the descriptions thereof).

Conventionally, a temperature of an object may be determined directly based on one or more images of the object acquired by an imaging device, and each of the images of the objects may be used for the temperature measurement of the object, although a portion of the one or more images may present interference areas (e.g., an ear of a human body) for the temperature measurement, which may decrease the efficiency and accuracy of temperature measurement. Further, after determining that a temperature of an object exceeds a threshold, temperature information of all points of each image of the object may be used to determine the temperature of the object, which increases the computing amount and costs more computing resources, thereby further decreasing the efficiency and accuracy of temperature measurement. In some occasions, when an object is moving, different images of an object acquiring by an imaging device may include different parts of the object. If temperatures of different parts of the object are different, the temperature of the object acquired based on the images including different parts of the object has a limited accuracy or is inaccurate. Merely by way of example, temperatures of different parts of a human being are different. For example, the temperature of ear area of a human being is usually higher than the temperature of the facial area or the forehead area. If the temperature of the face area or forehead area of a human being is used as the temperature of the human being, some images acquired by the imaging device may include less or even no the facial area or forehead area during walking, causing the temperature of the human being determined based on these images with a limited accuracy or inaccuracy.

In the process 500, the processing device 112A may determine an angle between the object and the imaging device when the image is acquired by the imaging device based on the image acquired by the imaging device, and determine the temperature of the object based on the image in response to determining that the angle satisfies a condition. Compared with a conventional temperature measurement approach which does not involve determining whether the images are suitable for determining the temperature of the object, some embodiments of the present disclosure may determine the temperature of the object only using the images that satisfies a condition (i.e., the angle between the object and the imaging device when the image is acquired by the imaging device satisfies a condition), In this way, images that do not satisfy the conditions may be filtered out and not be used to determine the temperature of the object, thereby improving the efficiency and accuracy of the determining of the temperature of the object.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include transmitting the temperature of the object to a terminal device (e.g., a terminal device 140) for display.

FIG. 6 is a schematic flowchart illustrating an exemplary process for determining a temperature of an object according to some embodiments of the present disclosure. In some embodiments, a process 600 may be implemented as a set of instructions (e.g., an application) stored in the storage device 150, ROM 230 or RAM 240, or storage 390. The processing device 112A, the processor 220, and/or the CPU 330 may execute the set of instructions, and when executing the instructions, the processing device 112A, the processor 220, and/or the CPU 330 may be configured to perform the process 600. The operations of the illustrated process presented below are intended to be illustrative. In some embodiments, the process 600 may be accomplished with one or more additional operations not described and/or without one or more of the operations discussed. Additionally, the order in which the operations of the process 600 illustrated in FIG. 6 and described below is not intended to be limiting. In some embodiments, one or more operations of the process 600 may be performed to achieve at least part of operation 507 as described in connection with FIG. 5.

In 601, the processing device 112A (e.g., determination module 420) may obtain a first image of an object that is acquired by a first imaging device.

In some embodiments, the first image does not include temperature information of the object. For example, the first imaging device may be a visible imaging device used to capture visible light information of a scene. The first image acquired by the first imaging device may be a visible image without temperature information of the object. In some embodiments, the operation 601 may be similar to or the same as the operation 501 of the process 500 as illustrated in FIG. 5, and the descriptions thereof are not repeated here. In some embodiments, an angle between the object and the first imaging device when the first image is acquired by the first imaging device may satisfy a condition. More descriptions for determining of the angle between the object and the first imaging device and whether the angle between the object and the first imaging device satisfies a condition may be found elsewhere in the present disclosure. See, e.g., operation 503 and operation 505 in FIG. 5, and relevant descriptions thereof.

In 603, the processing device 112A (e.g., determination module 420) may obtain a second image of the object that is acquired by a second imaging device.

In some embodiments, the second image may include temperature information of the object. For example, the second imaging device may be a thermal imaging device (e.g., a thermal infrared imaging device) used to obtain temperature information of a scene. The second image acquired by the second imaging device may be a thermal infrared image including temperature information. In some embodiments, the operation 603 may be similar to or the same as the operation 501 of the process 500 as illustrated in FIG. 5, and the descriptions thereof are not repeated here.

In some embodiments, a time interval between when the first image is acquired and when the second image is acquired may be smaller than a time threshold. For example, the first image and the second image may be acquired at the same time, i.e., the time interval between when the first image is acquired and when the second image is acquired may be equal to 0. In some embodiments, the time threshold may be set manually by a user according to an experience value or a default setting of the temperature measurement system 100, or determined by the processing device 112A according to an actual need, such as 1 second, 5 seconds, 7 seconds, or a larger or smaller value.

In 605, the processing device 112A (e.g., determination module 420) may determine a position of the target region of the object in the second image based on a position of a target region of the object in the first image and a transform relationship between a first coordinate system of the first imaging device and a second coordinate system of the second imaging device.

In some embodiments, the target region of the object may be identified from the second image. A temperature of the target region of the object may be an approximate representation of the temperature of the object. For example, for a human being, the target region may include at least one of a facial area or a forehead area. More descriptions for the target region of the object may be found elsewhere in the present disclosure. See, e.g., operation 507 in FIG. 5 and relevant descriptions thereof.

The first image may include a plurality of first pixels (or first voxels) corresponding to a plurality of physical points of the target region of the object, and the second image may include a plurality of second pixels (or second voxels) corresponding to a plurality of physical points of the target region of the object. Each of the plurality of first pixels (or first voxels) may correspond to one of plurality of second pixels (or second voxels), that is, a first pixel (or a first voxel) in the first image and a second pixel (or a second voxel) in the second image may correspond to a same physical point of the object.

In some embodiments, the processing device 112A may obtain position information of the target region of the object in the first image. The processing device 112A may determine the position information of the target region of the object in the second image by converting the position information of the target region of the object in the first image based on the transform relationship. For example, the processing device 112A may identify a first pixel (or a first voxel) corresponding to each physical point of the target region of the object from the first image using an image segmentation algorithm or an object detection algorithm. The processing device 112A may determine coordinates of each first pixel (or each first voxel) in the first image in the first coordinate system of the first imaging device. For each physical point of the object, the processing device 112A may determine coordinates of a second pixel (or a second voxel) corresponding to the physical point in the second coordinate system based on the coordinates of a first pixel (or each first voxel) corresponding to the physical point by performing a coordinate transformation according to the transform relationship between the first coordinate system and the second coordinate system. The processing device 112A may determine the position information of the target region of the object in the second image based on the coordinates of second pixels (or second voxels) corresponding to physical points of the target region of the object.

In some embodiments, the first coordinate system or the second coordinate system may be a 3D coordinate system or a 2D coordinate system. For example, the first coordinate system may be a 3D coordinate system including an $X_1'$-axis, a $Y_1'$-axis, and a $Z_1'$-axis based on the first imaging device and the second coordinate system may be a 3D coordinate system including an $X_2'$-axis, a $Y_2'$-axis, and a $Z_2'$-axis based on the second imaging device. As another example, the first coordinate system may be a 3D coordinate system including an $X_1'$-axis, a $Y_1'$-axis, and a $Z_1'$-axis based on the first imaging device and the second coordinate system may be a 2D coordinate system including an $X_2'$-axis and a $Y_2'$-axis based on the second imaging device. In some embodiments, the first coordinate system and the second coordinate system, and/or the transform relationship may be set manually by a user or a default setting of the temperature measurement system 100. In some embodiments, the first coordinate system, the second coordinate system, and/or the transform relationship between the first coordinate system and the second coordinate system may be adjusted based on calibration parameters determined by camera calibration. In some embodiments, the first coordinate system, the second coordinate system, and the transform relationship may be updated regularly.

In 607, the processing device 112A (e.g., determination module 420) may determine a temperature of the object based on the position of the target region of the object in the second image.

In some embodiments, each second pixel (or each second voxel) in the second image may correspond to temperature information of a physical point of the target region of the object. A relationship (e.g., a function) between the value of a second pixel (or second voxel) and a temperature represented by the second pixel (or second voxel) may be set according to a default setting of the system 100. The processing device 112A may determine the temperature information of each physical point of the target region of the object based on the values of second pixels of the second image and the relationship between the value of the second pixel (or second voxel) and a temperature represented by the second pixel (or second voxel). The processing device 112A may further determine the temperature of the object based on temperature information of one or more physical points of the target region of the object. For example, the processing device 112A may determine the maximum temperature of the target region as the temperature of the object. As another example, the processing device 112A may determine an average of temperatures of a plurality of physical points in the target region as the temperature of the object.

FIG. 7 is a schematic flowchart illustrating an exemplary process for generating a trained machine learning model according to some embodiments of the present disclosure. In some embodiments, a process 700 may be implemented as a set of instructions (e.g., an application) stored in the storage device 150, ROM 230 or RAM 240, or storage 390. The processing device 112B, the processor 220, and/or the CPU 330 may execute the set of instructions, and when executing the instructions, the processing device 112, the processor 220, and/or the CPU 330 may be configured to perform the process 700. In some embodiments, the trained machine learning model described in connection with operation 503 in FIG. 5 may be obtained according to the process 700. In some embodiments, the process 700 may be performed by another device or system other than the temperature measurement system 100, e.g., a device or system of a vendor or a manufacturer of the trained machine learning model. For illustration purposes, the implementation of the process 700 by the processing device 172 is described as an example.

In 701, the processing device 112B (e.g., the acquisition module 440) may obtain a plurality of training samples each of which includes a sample image of a sample object acquired by a sample imaging device, each of at least a portion of sample images being labeled with a sample angle between the sample object corresponding to the sample image and the sample imaging device.

In some embodiments, a sample object may be of a same type as the object as described in connection with operation 501. Two subjects may be deemed as being of a same type if they correspond to a same kind of a non-biological object or a biological object. For example, both of a sample object and the object as described in connection with operation 501 may be human beings. The sample imaging device may include any type of device that is capable of acquiring image data as described elsewhere in this disclosure (e.g., FIG. 1, FIG. 5, and the relevant descriptions), such as a camera (e.g., a digital camera, an analog camera, an IP camera (IPC), etc.), a video recorder, a scanner, a mobile phone, a tablet computing device, a wearable computing device, an infrared imaging device, or the like. A sample image of a sample object may be similar to the image of the object as described in connection with operation 501. In some embodiments, a sample image of a sample object may include a reference image of a reference object described in FIG. 5.

In some embodiments, a labeled sample angle may be similar to the angle between the object and the imaging device as described in connection with operation 501. A labeled sample angle between a sample object and a sample imaging device may be defined by a sample reference direction and a sample direction the sample object facing. The labeled sample angle between a sample object and a sample imaging device may be an angle between the sample reference direction of and the direction the sample object facing. As use herein, a direction that a sample object is facing refers to a direction substantially perpendicular to a sample target region or a sample target surface including the sample target region of the sample object and pointing outward. The sample target region of the sample object may be a region of interest of the sample object for temperature detection (or measurement). In other words, the temperature of the sample object may be detected from the sample target region of the sample object. For example, the sample object may include a human body or the head of the human body, and the sample target region may include the facial area or the forehead area of the human body. As another example, the sample object may include a back surface and a front surface, the front surface may be the sample target surface, and the direction that the sample object is facing may be from the back surface of the sample object pointing to the front surface of the sample object. Merely by way of example, if a front surface of a sample object is facial area, the direction that the sample object is facing refers to a direction from the back portion of the head of the sample object to the front portion (referred to as a face portion) of the head of the sample object.

In some embodiments, the sample reference direction may be related to a position relationship between the sample imaging device and the sample object. In some embodiments, the sample reference direction may be a direction of an optic axis of the sample imaging device pointing from a side of the sample imaging device facing the sample object to the sample imaging device. For example, if the sample object is located at the optic axis of the sample imaging device, the sample reference direction may be a direction of the optic axis of the sample imaging device pointing from a side of the sample imaging device facing the sample object to the sample imaging device. In some embodiments, the sample reference direction may be a direction of a reference line horizontally connecting the sample imaging device and the sample object, and the direction of the reference line may point from the sample object to the sample imaging device. For example, the reference line may be a horizontal line that passes through the geometric center point of the sample object and intersect a vertical line passing through the geometric center point of the sample imaging device. The range of the labeled sample angle between the sample object and the sample imaging device may be in a range from 0 degree to 180 degrees. A labeled sample angle may be determined using an angle measurement apparatus.

In some embodiments, the sample image in a training sample may be used as an input of the machine learning model, and the labeled sample angle corresponding to the sample image in the training sample may be used as a desired output of the machine learning model during a training process of the machine learning model.

In some embodiments, the processing device 140B may obtain a training sample (or a portion thereof) from one or more components of the temperature measurement system 100 (e.g., the storage device 150, the terminal devices(s) 140) or an external source (e.g., a database of a third-party) via a network (e.g., terminal the network 120).

In 703, the processing device 112B (e.g., the training module 450) may train a preliminary machine learning model using the plurality of training samples.

The preliminary machine learning model refers to a model to be trained. The preliminary machine learning model may be of any type of model as described elsewhere in this disclosure (e.g., FIG. 5 and the relevant descriptions). In some embodiments, the preliminary machine learning model may be a machine learning model that has been never trained using a training set. In some embodiments, the preliminary machine learning model may be a trained machine learning model that is trained using a training set including training samples that are different from the plurality of training samples obtained in operation 701. In some embodiments, the processing device 112B may obtain the preliminary machine learning model from one or more components of the temperature measurement system 100 (e.g., the storage device 150, the terminal device(s) 140) or an external source (e.g., a database of a third-party) via a network (e.g., the network 120).

In some embodiments, the preliminary machine learning model may be constructed based on a neural network model (e.g., a multilayer perceptron), a statistical model, or the like, or a combination thereof. In some embodiments, the preliminary machine learning model may include a multi-layer structure. For example, the preliminary machine learning model may include an input layer, an output layer, and one or more hidden layers between the input layer and the output layer. In some embodiments, the hidden layers may include one or more convolution layers, one or more rectified-linear unit layers (ReLU layers), one or more pooling layers, one or more fully connected layers, or the like, or any combination thereof. As used herein, a layer of a model may refer to an algorithm or a function for processing input data of the layer. Different layers may perform different kinds of processing on their respective input. A successive layer may use output data from a previous layer of the successive layer as input data. In some embodiments, the convolutional layer may include a plurality of kernels, which may be used to extract a feature. In some embodiments, each kernel of the plurality of kernels may filter a portion (i.e., a region). The pooling layer may take an output of the convolutional layer as an input. The pooling layer may include a plurality of pooling nodes, which may be used to sample the output of the convolutional layer, so as to reduce the computational load of data processing and accelerate the speed of data processing. In some embodiments, the size of the matrix representing the inputted data may be reduced in the pooling layer. The fully connected layer may include a plurality of neurons. The neurons may be connected to the pooling nodes in the pooling layer. In the fully connected layer, a plurality of vectors corresponding to the plurality of pooling nodes may be determined based on a training sample, and a plurality of weighting coefficients may be assigned to the plurality of vectors. The output layer may determine an output based on the vectors and the weighting coefficients obtained from the fully connected layer.

In some embodiments, each of the layers may include one or more nodes. In some embodiments, each node may be connected to one or more nodes in a previous layer. The number of nodes in each layer may be the same or different. In some embodiments, each node may correspond to an activation function. As used herein, an activation function of a node may define an output of the node given input or a set of inputs. In some embodiments, each connection between two of the plurality of nodes in the primary machine learning model may transmit a signal from one node to another node. In some embodiments, each connection may correspond to a weight. As used herein, a weight corresponding to a connection may be used to increase or decrease the strength or impact of the signal at the connection.

The primary machine learning model may include a plurality of parameters, such as architecture parameters, learning parameters, etc. Exemplary architecture parameters of the primary machine learning model may include the size of a kernel of a layer, the total count (or number) of layers, the count (or number) of nodes in each layer, a learning rate, a batch size, an epoch, etc. Exemplary learning parameters may include a connected weight between two connected nodes, a bias vector relating to a node, etc.). Before the training, the primary machine learning model may have one or more initial parameter values. In the training of the primary machine learning model, learning parameters of the primary machine learning model may be updated. Before the updating process, values of the learning parameters of the primary machine learning model may be initialized. For example, the connected weights and/or the bias vector of nodes of the primary machine learning model may be initialized by assigning random values in a range, e.g., the range from −1 to 1. As another example, all the connected weights of the primary machine learning model may be assigned the same value in the range from −1 to 1, for example, 0. As still an example, the bias vector of nodes in the primary machine learning model may be initialized by assigning random values in a range from 0 to 1. In some embodiments, the parameters of the primary machine learning model may be initialized based on a Gaussian random algorithm, a Xavier algorithm, etc.

In some embodiments, the processing device 112B may train the preliminary machine learning model using a training algorithm to obtain the trained machine learning model. Exemplary training algorithms may include a backpropagation algorithm, a gradient descent algorithm, a Newton's algorithm, a quasi-Newton algorithm, a Levenberg-Marquardt algorithm, a conjugate gradient algorithm, or the like, or a combination thereof.

The training of the preliminary machine learning model may include one or more iterations to iteratively update the model parameters of the preliminary machine learning model based on the training sample(s) until a termination condition is satisfied in a certain iteration. Exemplary termination conditions may be that the value of a loss function obtained in the certain iteration is less than a threshold value, that a certain count of iterations has been performed, that the loss function converges such that the difference of the values of the loss function obtained in a previous iteration and the current iteration is within a threshold value, etc. The loss function may be used to measure a discrepancy between a sample angle between the sample object corresponding to the sample image and the sample imaging device predicted by the preliminary machine learning model in an iteration and the labeled sample angle. For example, the sample image of each training sample may be inputted into the preliminary machine learning model. The preliminary machine learning model may extract features associated with the sample angle from the sample image. For example, the preliminary machine learning model may extract the features associated with the sample angle in a similar manner as how to the features associated with the angle are be extracted from the image as described in operation 503. The preliminary machine learning model may determine the sample angle based on the features associated with the sample angle, and output predicted sample angle of the sample image of the training sample. The loss function may be used to measure a difference between the predicted sample angle and the labeled sample angle of each training sample. Exemplary loss functions may include a focal loss function, a log loss function, a cross-entropy loss, a Dice ratio, or the like. If the termination condition is not satisfied in the current iteration, the processing device 112B may further update the preliminary machine learning model to be used in a next iteration according to, for example, a backpropagation algorithm. If the termination condition is satisfied in the current iteration, the processing device 112B may designate the preliminary machine learning model in the current iteration as the trained machine learning model.

The trained machine learning model (e.g., the second portion of the trained machine learning model) may provide a corresponding relationship between sample image of the sample object in each training sample and the sample angle between the sample object and the sample imaging device. The trained machine learning model may include multiple pairs of sample image and sample angle. As used herein, the corresponding relationship may refer to that the sample image corresponds to the sample angle.

Figure 8:
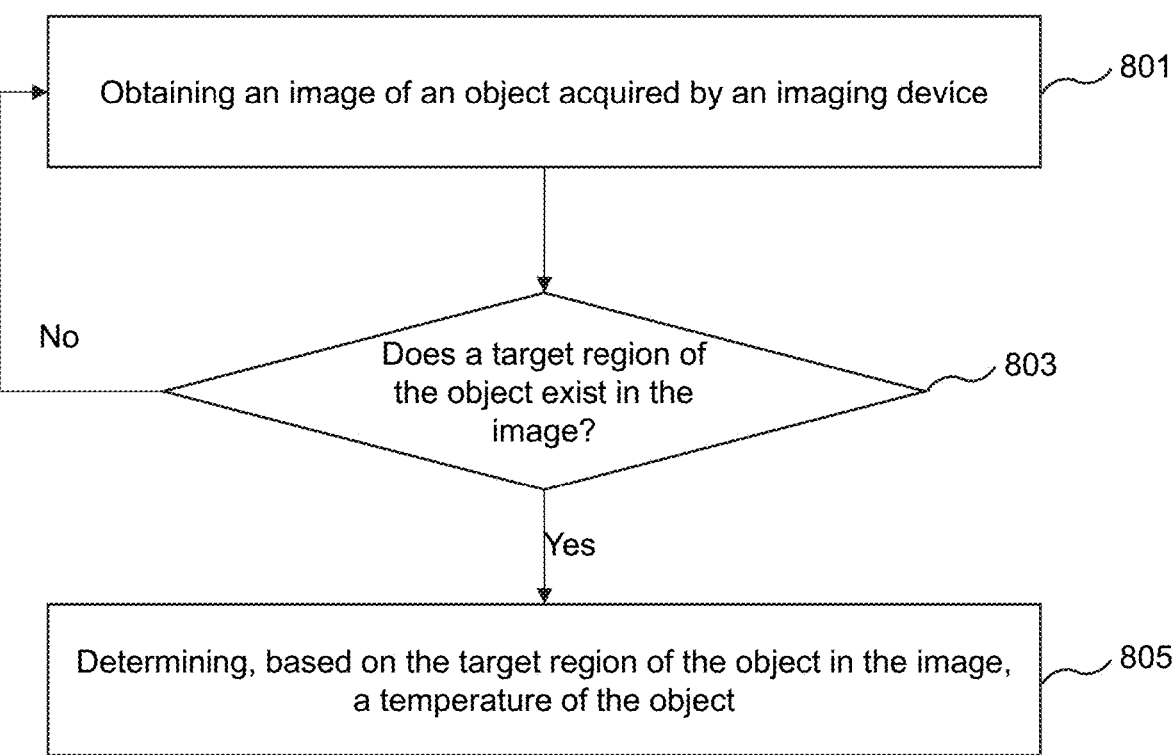
FIG. 8 is a schematic flowchart illustrating an exemplary process for determining a temperature of an object according to some embodiments of the present disclosure.

FIG. 8 is a schematic flowchart illustrating an exemplary process for determining a temperature of an object according to some embodiments of the present disclosure. In some embodiments, a process 800 may be implemented as a set of instructions (e.g., an application) stored in the storage device 150, ROM 230 or RAM 240, or storage 390. The processing device 112A, the processor 220, and/or the CPU 330 may execute the set of instructions, and when executing the instructions, the processing device 112A, the processor 220, and/or the CPU 330 may be configured to perform the process 800. The operations of the illustrated process presented below are intended to be illustrative. In some embodiments, the process 800 may be accomplished with one or more additional operations not described and/or without one or more of the operations discussed. Additionally, the order in which the operations of the process 800 illustrated in FIG. 8 and described below is not intended to be limiting.

In 801, the processing device 112A (e.g., the acquisition module 410) may obtain an image of an object acquired by an imaging device.

In some embodiments, the image may include a thermal infrared image, a visible image, or any other type of images. In some embodiments, the imaging device may include any type of device that is capable of acquiring image data as described elsewhere in this disclosure (e.g., FIG. 1 and the relevant descriptions), such as a camera (e.g., a digital camera, an analog camera, an IP camera (IPC), etc.), a video recorder, a scanner, a mobile phone, a tablet computing device, a wearable computing device, an infrared imaging device, or the like. In some embodiments, the operation 801 may be similar to or the same as the operation 501 of the process 500 as illustrated in FIG. 5, the descriptions of which are not repeated here.

In 803, the processing device 112A (e.g., the determination module 420) may determine whether a target region of the object exists in the image.

A temperature of the target region of the object may be an approximate representation of the temperature of the object. For example, for a human being, the target region may include at least one of a facial area or a forehead area.

In some embodiments, the target region of the object may be identified from the image in a similar manner as how to a target region of an object is identified from an image described in connection with operation 507 in FIG. 5, and the description of which are not repeated here.

In response to a determination that the target region of the object does not exist in the image, the processing device 112A may proceed to perform operation 801. The processing device 112A may obtain an additional image (or a next image) of the object acquired by the imaging device, and assess the target region of the object.

In response to a determination that the target region of the object exists in the image, the processing device 112A may proceed to perform operation 805.

In some embodiments, in response to a determination that the target region of the object exists in the image, the processing device 112A may further determine whether the target region of the object represented in the image satisfies a condition (also referred to as a third condition). Whether the target region of the object represented in the image satisfies the third condition may be determined based on an area of the target region of the object in the image, a shape of the target region of the object in the image, and/or the position of the target region in the image. In some embodiments, the processing device 112A may determine whether the area of the target region is larger than or equal to an area threshold. The processing device 112A may determine that the target region of the object represented in the image satisfies the third condition if the area of the target region is larger than or equal to the area threshold. In some embodiments, the area threshold may be determined according to, such as a type of the object, a type of the target region of the object used to determine a temperature of the object, etc. For example, different area thresholds may need to be determined for different types of objects. As another example, different area thresholds may need to be determined for different target regions of a same type of object. In some embodiments, the area threshold may be set manually by a user according to an experience value or a default setting of the temperature measurement system 100, or determined by the processing device 112A according to an actual need. In some embodiments, the processing device 112A may determine whether the shape of the target region matches a reference shape of the target region. The processing device 112A may determine that the target region of the object represented in the image satisfies the third condition if the shape of the target region matches the reference shape of the target region. The shape of the target region matching the reference shape of the target region may include a similarity between the shape of the target region and the reference shape of the target region exceeding a similarity threshold (e.g., 90%). The processing device 112A may determine that the target region of the object represented in the image satisfies the third condition if the position of the target region in the image is located in a reference region in the image. In some embodiments, the reference region may include a central region of the image.

In response to a determination that the target region of the object represented in the image does not satisfy the third condition, the processing device 112A may proceed to perform operation 801. The processing device 112A may obtain an additional image (or a next image) of the object acquired by the imaging device, and assess the target region of the object.

In response to a determination that the target region of the object represented in the image satisfies the third condition, the processing device 112A may proceed to perform operation 805.

In 805, the processing device 112A (e.g., the determination module 420) may determine, based on the target region of the object in the image, a temperature of the object.

In some embodiments, the processing device 112A may determine the temperature of the object based on temperature information of the target region. For example, the processing device 112A may determine the maximum temperature of the target region as the temperature of the object. As another example, the processing device 112A may determine an average of temperatures represented by a plurality of pixel points or voxel points in the target region as the temperature of the object. More descriptions for the determining of the temperature of the object may be found elsewhere in the present disclosure. See, e.g., operation 507 in FIG. 5 and relevant descriptions thereof.

Figure 9:
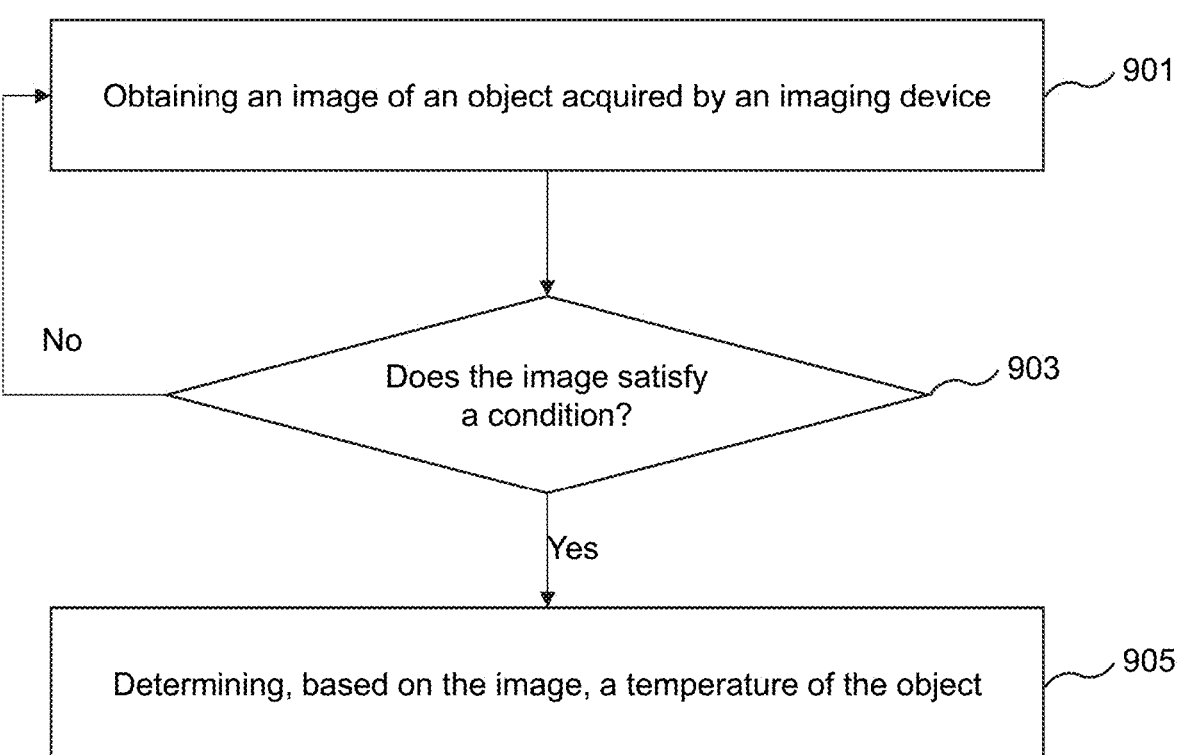
FIG. 9 is a schematic flowchart illustrating an exemplary process for determining a temperature of an object according to some embodiments of the present disclosure.

FIG. 9 is a schematic flowchart illustrating an exemplary process for determining a temperature of an object according to some embodiments of the present disclosure. In some embodiments, a process 900 may be implemented as a set of instructions (e.g., an application) stored in the storage device 150, ROM 230 or RAM 240, or storage 390. The processing device 112A, the processor 220, and/or the CPU 330 may execute the set of instructions, and when executing the instructions, the processing device 112A, the processor 220, and/or the CPU 330 may be configured to perform the process 900. The operations of the illustrated process presented below are intended to be illustrative. In some embodiments, the process 900 may be accomplished with one or more additional operations not described and/or without one or more of the operations discussed. Additionally, the order in which the operations of the process 900 illustrated in FIG. 9 and described below is not intended to be limiting.

In 901, the processing device 112A (e.g., the acquisition module 410) may obtain an image of an object acquired by an imaging device.

In some embodiments, the image may include a thermal infrared image, a visible image, or any other type of images. In some embodiments, the imaging device may include any type of device that is capable of acquiring image data as described elsewhere in this disclosure (e.g., FIG. 1 and the relevant descriptions), such as a camera (e.g., a digital camera, an analog camera, an IP camera (IPC), etc.), a video recorder, a scanner, a mobile phone, a tablet computing device, a wearable computing device, an infrared imaging device, or the like. In some embodiments, the operation 901 may be similar to or the same as the operation 501 of the process 500 as illustrated in FIG. 5, the descriptions of which are not repeated here.

In 903, the processing device 112A (e.g., the determination module 420) may determine whether the image satisfies a condition (also referred to as a first condition).

In some embodiments, the image satisfying the first condition may include that an angle between the object and the imaging device when the image is acquired by the imaging device satisfies a condition (also referred to as a second condition). The processing device 112A may determine the angle between the object and the imaging device based on the image, and determine whether the angle between the object and the imaging device satisfies the second condition. In some embodiments, the determining of the angle between the object and the imaging device and whether the angle satisfies the second condition may be similar to or the same as the operation 503 and the operation 505 of the process 500 as illustrated in FIG. 5, the descriptions of which are not repeated here.

In some embodiments, the image satisfying the condition may include that a target region of the object exists in the image and/or the target region satisfies a third condition (e.g., the area of the target region exceeds an area threshold) as described in FIG. 8. The processing device 112A may determine whether the target region of the object exists in the image and/or whether the target region satisfies the third condition according to operation 803 of the process 800 as illustrated in FIG. 8, the descriptions of which are not repeated here.

In some embodiments, the image satisfying the first condition may include that the target region of the object exists in the image and an interference region of the object does not exist in the image. The interference region of the object may refer to an invalid portion of the object for temperature measurement. For example, the object may include the head of a human body, the target region of the object may include the facial area and/or the forehead area, and the interference region of the object may include the ears. In some embodiments, the interference region of the object may be identified from the image in a similar manner as how to a target region of an object is identified from an image described in connection with operation 507 in FIG. 5, and the description of which are not repeated here. In some embodiments, the target region and/or the interference region of the object may be set by a user according to actual requirements or according to a default setting of the system 100.

In some embodiments, the processing device 112A may determine whether the image satisfies the first condition by inputting the image into a trained machine learning model. The trained machine learning model may output a result indicating whether the image satisfies the first condition. The trained machine learning model may be used to assess whether the image is qualified for temperature measurement. The trained machine learning model may be obtained by training a preliminary machine learning model using a plurality of sample images. In some embodiments, the plurality of sample images may include positive samples each of which is annotated with a label of "positive sample" (e.g., value 1). A positive sample may include a sample image that satisfies the first condition. The accuracy of a temperature determined based on the positive sample may be higher. In some embodiments, the plurality of sample images may include negative samples each of which is annotated with a label of "negative sample" (e.g., value 0). A negative sample may include a sample image that does not satisfy the first condition. The accuracy of a temperature determined based on the negative sample may be lower. In the training of the preliminary machine learning model for assessing an image, the plurality of sample images may serve as inputs of the preliminary machine learning model and the labels corresponding to the plurality of sample images may serve as desired outputs. The preliminary machine learning model may be trained to decrease a deviation between an actual output generated based on an input (i.e., a sample image) and a desired output (i.e., the label) corresponding to the input. The preliminary machine learning model may be trained to learn whether a specific image satisfies the first condition for temperature measurement. In some embodiments, the plurality of sample images may be or include the plurality of reference images as described elsewhere in the present disclosure. More descriptions for the training of the preliminary machine learning model may be found elsewhere in the present disclosure (e.g., FIG. 7 and the descriptions thereof).

In response to a determination that the image does not satisfy the first condition, the processing device 112A may proceed to perform operation 901. The processing device 112A may obtain an additional image (or a next image) of the object acquired by the imaging device, and assess whether the additional image (or the next image) satisfies the first condition.

In response to a determination that the image of the object satisfies the first condition, the processing device 112A may proceed to perform operation 905.

In 905, the processing device 112A (e.g., the determination module 420) may determine, based on the image, a temperature of the object.

In some embodiments, a target region of the object may be identified from the image. A temperature of the target region may be an approximate representation of the temperature of the object. For example, for a human being, the target region may include at least one of a facial area or a forehead area. In some embodiments, the operation 905 may be similar to or the same as the operation 507 of the process 500 as illustrated in FIG. 5, the descriptions of which are not repeated here.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:

at least one storage device including a set of instructions; and at least one processor in communication with the at least one storage device, wherein when executing the set of instructions, the at least one processor is directed to perform operations including:

obtaining an image of an object acquired by an imaging device;

determining, based on the image, an angle between the object and the imaging device, the angle being defined by a reference direction and a direction that the object is facing; and determining, based on the image, a temperature of the object in response to determining that the angle satisfies a condition, including:

obtaining a second image of the object acquired by a second imaging device, the second image being a thermal image and including temperature information of the object;

determining a position of the object in the second image based on a position of the object in the image and a transform relationship between a first coordinate system of the imaging device and a second coordinate system of the second imaging device;

obtaining, based on the position of the object in the second image, the temperature information of the object; and determining, based on the temperature information of the object, the temperature of the object.

2. The system of claim 1, wherein the determining, based on the image, an angle between the object and the imaging device includes:

determining, based on the image, the angle between the object and the imaging device using an angle detection model associated with a plurality of reference images of reference objects each of which is acquired by a reference imaging device and corresponds to a reference angle between a reference object and the reference imaging device.

3. The system of claim 2, wherein the angle detection model includes a trained machine learning model, and the trained machine learning model is acquired according to a training process including:

obtaining the plurality of reference images of reference objects;

labeling each of at least a portion of the plurality of reference images with the reference angle corresponding to the reference image; and training a preliminary machine learning model using the plurality of reference images and the reference angles corresponding to the plurality of reference images.

4. The system of claim 3, wherein the determining, based on the image, an angle between the object and the imaging device includes:

inputting the image into the trained machine learning model;

extracting image features from the image using the trained machine learning model; and determining the angle based on the image features from the image.

5. The system of claim 2, wherein the angle detection model includes a corresponding relationship between each of the plurality of reference images of reference objects and the reference angle between the reference object and the imaging device, and the determining, based on the image, an angle between the object and the imaging device using an angle detection model includes:

extracting angle features from the image;

extracting reference angle features from each of the plurality of reference images;

determining at least one of the plurality of reference images whose reference angle features match the angle features of the image; and determining the angle between the object and the imaging device based on at least one reference angle corresponding to the at least one of the plurality of reference images.

6. The system of claim 1, wherein the obtaining, based on the position of the object in the second image, the temperature information of the object includes:

identifying a target region of the object from the second image based on the position of the object in the second image; and determining temperature information of the target region.

7. The system of claim 6, wherein the target region includes at least one of a facial area or a forehead area.

8. The system of claim 6, wherein the determining, based on temperature information of the target region, the temperature of the object includes:

determining a bounding box enclosing the target region, the bounding box being defined by at least one of one or more geometric parameters and position parameters; and determining the temperature of the object based on the temperature information of the target region enclosed by the bounding box.

9. A system, comprising:

at least one storage device including a set of instructions; and at least one processor in communication with the at least one storage device, wherein when executing the set of instructions, the at least one processor is directed to perform operations including:

obtaining an image of an object acquired by an imaging device;

determining whether the image satisfies a condition; and determining, based on the image, a temperature of the object in response to determining that the image satisfies the condition, including:

obtaining a second image of the object acquired by a second imaging device, the second image being a thermal image and including temperature information of the object;

determining a position of the object in the second image based on a position of the object in the image and a transform relationship between a first coordinate system of the imaging device and a second coordinate system of the second imaging device;

obtaining, based on the position of the object in the second image, the temperature information of the object; and determining, based on the temperature information of the object, the temperature of the object.

10. A method, the method being implemented on a computing device having at least one storage device and at least one processor, the method comprising:

obtaining an image of an object acquired by an imaging device;

determining, based on the image, an angle between the object and the imaging device, the angle being defined by a reference direction and a direction that the object is facing; and determining, based on the image, a temperature of the object in response to determining that the angle satisfies a condition.

11. The method of claim 10, wherein the determining, based on the image, an angle between the object and the imaging device includes:

determining, based on the image, the angle between the object and the imaging device using an angle detection model associated with a plurality of reference images of reference objects each of which is acquired by a reference imaging device and corresponds to a reference angle between a reference object and the reference imaging device.

12. The method of claim 11, wherein the angle detection model includes a trained machine learning model, and the trained machine learning model is acquired according to a training process including:

obtaining the plurality of reference images of reference objects;

labeling each of at least a portion of the plurality of reference images with the reference angle corresponding to the reference image; and training a preliminary machine learning model using the plurality of reference images and the reference angles corresponding to the plurality of reference images.

13. The method of claim 12, wherein the determining, based on the image, an angle between the object and the imaging device includes:

inputting the image into the trained machine learning model;

extracting image features from the image using the trained machine learning model; and determining the angle based on the image features from the image.

14. The method of claim 11, wherein the angle detection model includes a corresponding relationship between each of the plurality of reference images of reference objects and the reference angle between the reference object and the imaging device, and the determining, based on the image, an angle between the object and the imaging device using an angle detection model includes:

extracting angle features from the image;

extracting reference angle features from each of the plurality of reference images;

determining at least one of the plurality of reference images whose reference angle features match the angle features of the image; and determining the angle between the object and the imaging device based on at least one reference angle corresponding to the at least one of the plurality of reference images.

15. The method of claim 10, identifying a target region of the object from a second image based on a position of the object in the second image; and determining temperature information of the target region.

16. The method of claim 15, wherein the target region includes at least one of a facial area or a forehead area.

17. The method of claim 15, wherein the determining, based on temperature information of the target region, the temperature of the object includes:

determining a bounding box enclosing the target region, the bounding box being defined by at least one of one or more geometric parameters and position parameters; and determining the temperature of the object based on the temperature information of the target region enclosed by the bounding box.

* * * * *